(12) United States Patent
Bevill et al.

(10) Patent No.: US 9,120,766 B2
(45) Date of Patent: Sep. 1, 2015

(54) METHODS OF MAKING COCRYSTALS

(71) Applicant: Aptuit (West Lafayette), LLC, Wilmington, DE (US)

(72) Inventors: Melanie Janelle Bevill, West Lafayette, IN (US); Christopher Scott Seadeek, West Lafayette, IN (US); Ekaterina V. Albert, West Lafayette, IN (US); Petinka I. Vlahova, West Lafayette, IN (US); Richard James Ely, Williamsport, IN (US); Patricia Andres, West Lafayette, IN (US)

(73) Assignee: AMRI SSCI, LLC, West Lafayette, IN (US)

( * ) Notice: Subject to any disclaimer, the term of this patent is extended or adjusted under 35 U.S.C. 154(b) by 0 days.

(21) Appl. No.: 13/657,259

(22) Filed: Oct. 22, 2012

(65) Prior Publication Data

US 2013/0102781 A1    Apr. 25, 2013

Related U.S. Application Data

(60) Provisional application No. 61/550,341, filed on Oct. 21, 2011.

(51) Int. Cl.
| | | |
|---|---|---|
| *C30B 7/08* | (2006.01) | |
| *C07J 9/00* | (2006.01) | |
| *A61K 31/575* | (2006.01) | |
| *A61K 31/60* | (2006.01) | |
| *C07D 401/04* | (2006.01) | |
| *C07D 213/82* | (2006.01) | |
| *C07D 239/50* | (2006.01) | |
| *C07D 473/12* | (2006.01) | |
| *C30B 29/54* | (2006.01) | |
| *C07C 51/43* | (2006.01) | |

(52) U.S. Cl.
CPC .............. *C07D 401/04* (2013.01); *C07C 51/43* (2013.01); *C07D 213/82* (2013.01); *C07D 239/50* (2013.01); *C07D 473/12* (2013.01); *C30B 7/08* (2013.01); *C30B 29/54* (2013.01)

(58) Field of Classification Search
USPC ..................... 544/323; 117/68; 514/177, 164
See application file for complete search history.

(56) References Cited

U.S. PATENT DOCUMENTS

| | | | |
|---|---|---|---|
| 7,452,555 B2 | 11/2008 | Childs | |
| 8,212,079 B2 | 7/2012 | Childs | |
| 8,350,085 B2 | 1/2013 | Childs | |
| 2011/0251426 A1 | 10/2011 | Childs et al. | |
| 2014/0073674 A1 | 3/2014 | Bevill et al. | |
| 2014/0035595 A1 | 8/2014 | Albert et al. | |

OTHER PUBLICATIONS

Breuil, A.C. et al., "Characterization of a Pterostilbene Dehydrodimer Produced by Laccase of *Botrytis cinerea*," *Phytopathology* vol. 89, No. 4, pp. 298-302 (1999).
Etter, Margaret C. et al., "Graph-Set Analysis of Hydrogen-Bond Patterns in Organic Crystals," *Acta Cryst.*, B46, pp. 256-262 (1990).
Etter, Margaret C. et al., "The use of Cocrystallization as a Method of studying Hydrogen Bond Preferences of 2-Aminopyridine," *Journal of the Chemical Society, Chemical Communications*, No. 8, pp. 589-591 (1990).
Flack, H.D., "On Enantiomorph-Polarity Estimation," *Acta Cryst.*, A39, pp. 876-881 (1983).
Gorbötz, C.H. et al., "On the inclusion of solvent molecules in the crystal structures of organic compounds," *Acta Cryst.*, B56, pp. 526-534, (2000).
Hooft, R.W.W. et al., "Determination of absolute structure using Bayesian statistics on Bijvoet differences", *J. Appl. Cryst.*, vol. 41, pp. 96-103 (2008).
Kumar et al., "Molecular Complexes of Some Mono- and Dicarboxylic Acids with trans-1,4-Dithiane-1,4-dioxide," *American Chemical Society, Crystal Growth & Design*, vol. 2, No. 4, pp. 313-318, (2002).
Pezet, R., "Purification and characterization of a 32-kDa laccase-like stilbene oxidase produced by *Botrytis cinerea* Pers.:Fr.," FEMS Microbiology Letters, vol. 167, pp. 203-208, (1998).
Schultheiss, N. et al., "Nutraceutical cocrystals: utilizing pterostilbene as a cocrystal former," *Crystal Engineering Communications*, vol. 12, pp. 2436-2442, (2010).
Schultheiss, N. et al., "Attempted construction of minoxidil: carboxylic acid cocrystals; 7 salts and 1 cocrystal resulted," *Crystal Engineering Communications*, vol. 12, pp. 742-749 (2010).
Schultheiss, N. et al., "Attempted construction of minoxidil: carboxylic acid cocrystals; 8 salts and 1 cocrystal resulted," *Crystal Engineering Communications*, Supplementary Material, pp. 1-19 (2010).
Schultheiss, N. et al., "Nifedipine—pyrazine (2/1)," *Acta Cryst.* E66, pp. o2297-o2298 (2010).
David C. Lee and Michael L. Webb, Pharmaceutical Analysis, 2003, pp. 254-259, 1st edition, CRC Press, Boca Raton, Florida, United States of America.
Nate Schultheiss, et al, Cocrystals of nutraceutical p-coumaric acid with caffeine and theophylline: polymorphism and solid-state stability explored in detail using their crystal graphs, CrystEngComm, Sep. 22, 2010, pp. 611-619, 13, The Royal Society of Chemistry, London, United Kingdom.

*Primary Examiner* — Kristin Vajda
(74) *Attorney, Agent, or Firm* — D'Hue Law LLC; Cedric A. D'Hue

(57) ABSTRACT

Disclosed are processes for preparing cocrystals, including processes for scaling up of cocrystal formation, as well as scalable processes for preparing cocrystals. Also disclosed are processes for scaled-up preparation of pterostilbene, progesterone, p-coumaric, and minoxidil cocrystals. Minoxidil cocrystals, such as minoxidil:benzoic acid 1:1 monohydrate cocrystals are also disclosed herein.

15 Claims, 25 Drawing Sheets

METHODS OF MAKING COCRYSTALS

TECHNICAL FIELD

The disclosure relates to processes for making cocrystals, including processes for scaling up of cocrystal formation, as well as to scalable processes for preparing cocrystals. In at least one embodiment, the disclosure relates to scaling up processes for preparing pterostilbene, p-coumaric, minoxidil, and progesterone cocrystals. Also disclosed herein are minoxidil cocrystals, such as minoxidil:benzoic acid cocrystals.

BACKGROUND

Cocrystals are crystals that contain two or more non-identical molecules. Examples of cocrystals may be found in the Cambridge Structural Database. Examples of cocrystals may also be found at Etter, Margaret C., and Daniel A. Adsmond (1990) "The use of cocrystallization as a method of studying hydrogen bond preferences of 2-aminopyridine" J. Chem. Soc., Chem. Commun. 1990 589-591, Etter, Margaret C., John C. MacDonald, and Joel Bernstein (1990) "Graph-set analysis of hydrogen-bond patterns in organic crystals" Acta Crystallogr., Sect. B, Struct. Sci. B46 256-262, Etter, Margaret C., Zofia Urba czyk-Lipkowska, Mohammad Zia-Ebrahimi, and Thomas W. Panunto (1990b) "Hydrogen bond directed cocrystallization and molecular recognition properties of diarylureas" J. Am. Chem. Soc. 112 8415-8426, which are incorporated herein by reference in their entireties.

The following articles are also incorporated herein by reference in their entireties: Carl Henrik Gorbotz and Hans-Petter Hersleth, 2000, "On the inclusion of solvent molecules in the crystal structures of organic compounds"; Acta Cryst. (2000), B56, 625-534; and V. S. Senthil Kumar, Ashwini Nangia, Amy K. Katz and H. L. Carrell, 2002, "Molecular Complexes of Some Mono- and Dicarboxylic Acids with trans-1,4,-Dithiane-1,4-dioxide" American Chemical Society, Crystal Growth & Design, Vol. 2, No. 4, 2002.

By cocrystallizing a compound with another compound, referred to as a "coformer", one creates a new solid form which has unique properties compared with existing solid forms of that compound. For example, a cocrystal may have different dissolution and solubility properties than the compound itself or as a salt. In the pharmaceutical field, the compound is often known as an active pharmaceutical ingredient ("API"), and the other component of the cocrystal (the coformer) is often a pharmaceutically acceptable compound (which could also be an API). Cocrystals containing APIs can be used to deliver APIs therapeutically. New drug formulations comprising cocrystals of APIs with pharmaceutically acceptable coformers may have superior properties over existing drug formulations. Compounds and coformers may also include, by way of example only, nutraceuticals, agricultural chemicals, pigments, dyes, explosives, polymer additives, lubricant additives, photographic chemicals, and structural and electronic materials.

When the compound, such as an API, is a hydrochloride (HCl) salt, for example, one can cocrystallize the HCl salt with a neutral coformer molecule. By doing this, one can create a cocrystal with specific properties. For instance one can make a cocrystal comprising an active pharmaceutical ingredient having greater or lesser intrinsic solubility and/or a faster or slower dissolution rate, depending on the coformer compound that is chosen.

By "coformer" what is meant is the component of the cocrystal that is not the compound of the cocrystal. The coformer is present in order to form the cocrystal with the compound. Thus, the coformer is part of the crystal lattice. It is contemplated that one or more coformers may be employed in a cocrystal, according to any of the techniques of the disclosure. Accordingly, the coformer is not required to have an activity of its own, although it may have some activity. In some situations, the coformer may have the same activity as or an activity complementary to that of the compound.

For example, some coformers may facilitate the therapeutic effect of an active pharmaceutical ingredient. For pharmaceutical formulations, the coformer may be any pharmaceutically acceptable molecule that forms a cocrystal with the API or its salt. The Registry of Toxic Effects of Chemical Substances (RTECS) database is a useful source for toxicology information, and the GRAS list contains about 2500 relevant compounds. Both sources may be used to help identify suitable coformers.

The coformer may be non-ionized, such as, for example, benzoic acid, succinic acid, and caffeine, or zwitterionic, such as, for example, L-lysine, L-arginine, or L-proline, or may be a salt, such as, for example, sodium benzoate or sodium succinate. Coformers may include, but are not limited to, organic bases, organic salts, alcohols, aldehydes, amino acids, sugars, ionic inorganics, carboxylic acids, amines, flavoring agents, sweeteners, nutraceuticals, aliphatic esters, aliphatic ketones, organic acids, aromatic esters, alkaloids, and aromatic ketones. In at least certain embodiments, the coformer may be a carboxylic acid or an alkaloid. Typically, coformers will have the ability to form complementary non-covalent interactions with the compound or its salt, including APIs and salts thereof, for example the ability to form hydrogen bonds with the compound or its salt.

Properties of compounds or their salts, such as APIs or salts thereof, may be modified by forming a cocrystal. Such properties include, for example, melting point, density, hygroscopicity, crystal morphology, loading volume, compressibility, and shelf life. Furthermore, other properties such as bioavailability, dissolution, solubility, toxicity, taste, physical stability, chemical stability, production costs, and manufacturing method may be modified by using a cocrystal, rather than the API alone or as a salt.

A compound, such as an API, can be screened for possible cocrystals, for example where polymorphic forms, hydrates, or solvates do not readily form from the compound. For example, a neutral compound that can only be isolated as amorphous material could be cocrystallized. Forming a cocrystal may improve the performance of a drug formulation of an API, for example by changing one or more properties identified earlier. A cocrystal may also optionally be used to isolate or purify a compound during manufacturing. If it is desirable to identify all of the solid state phases of an active pharmaceutical ingredient, then cocrystallization may be particularly desirable.

While much interest has been paid to preparing cocrystals of APIs and other compounds such as nutraceuticals, a recurring challenge has been the ability to prepare cocrystals in sufficient quantity or scale for commercialization. When cocrystals are prepared in a laboratory, techniques, such as with seeds or non-solvent approaches used to screen for the cocrystals, are typically not scalable and yields are in the milligram scale. Further, reports by others have shown thermodynamic and kinetic limitations for using solvent-based approaches. In particular, the inability to obtain congruent dissolution with compounds and coformers in a solvent has been a barrier to successful and reproducible scaled-up manufacture of cocrystals (Chiarella). Such dissolution problems are especially acute when the solubilities of the compound and the coformer differ substantially in the solvent selected. Thus, there is a need to develop a process whereby cocrystals can be scaled-up to at least gram-scale quantities.

By way of example only, both resveratrol and pterostilbene have been reported to exhibit a range of biological activities including anti-cancer, antioxidant, anti-inflammatory and other potential health benefits. Pterostilbene is found in nature in a variety of grapes and berries as well as plants commonly used in traditional folk medicine. Significant interest in pterostilbene has been generated in recent years due to its perceived health benefits, leading to increased consumption of foods that contain the compound such as grapes and berries.

Pterostilbene has, however, been noted to have poor solubility in water, making it difficult to incorporate in food extracts or supplements ("nutraceuticals") (López-Nicolás, J. M.; Rodriguez-Bonilla, P.; Méndez-Cazorla, L.; Garcia-Carmona, F., Physicochemical Study of the Complexation of Pterostilbene by Natural and Modified Cyclodextrins. *Journal of Agricultural and Food Chemistry* 2009, 57, (12), 5294-5300.). In addition, pterostilbene exhibits poor bioavailability and is easily oxidized by various enzymes (Pezet, R., Purification and characterization of a 32-kDa laccase-like stilbene oxidase produced by *Botrytis cinerea*. *FEMS Microbiol. Lett.* 1998, 167, 203-208 and Breuil, A. C.; Jeandet, P.; Adrian, M.; Chopin, F.; Pirio, N.; Meunier, P.; Bessis, R., Characterization of a pterostilbene dehydrodimer produced by laccase of *Botrytis cinerea*. *Phytopathology* 1999, 89, (298-302).). The melting point has been reported as 82° C. (Mallavadhani, U. V.; Sahu, G., Pterostilbene: A Highly Reliable Quality-Control Marker for the Ayurvedic Antidiabetic Plant 'Bijasar'. *Chromatographia* 2003, 58, 307-312.). Efforts to improve the solubility of pterostilbene have focused on formulation approaches, such as by using cyclodextrins (LoI 2009).

Recently, cocrystals and polymorphs of pterostilbene have been reported in WO/2011/09372, which is herein incorporated by reference.

SUMMARY

The disclosure relates, in various embodiments, to processes for preparing cocrystals, including scalable processes and processes for preparing scaled-up cocrystals. Exemplary processes may maintain congruent dissolution during the crystallization process. In further embodiments, the disclosure relates to the scaling up of pterostilbene cocrystals, such as, for example, pterostilbene:caffeine cocrystals and pterostilbene:piperazine cocrystals; progesterone cocrystals, such as progesterone:vanillic acid and progesterone cinnamic acid cocrystals; p-coumaric acid crystals, such as p-coumaric: nicotinamide cocrystals; and minoxidil cocrystals, such as minoxidil:benzoic acid cocrystals.

According to one aspect of the disclosure, processes for making a cocrystal of a compound and a coformer are described, comprising combining the compound dissolved in a solvent solution with the coformer dissolved in the solvent solution, wherein the solubilities of the compound and the coformer in the solvent solution are approximately equal and wherein the resulting cocrystal is crystallized from the solution.

According to another aspect of the disclosure, processes for making a cocrystal of a compound and a coformer are described, comprising combining the compound dissolved in a solvent solution with the coformer dissolved in the solvent solution, wherein the resulting cocrystal is crystallized from the solvent solution wherein the solubilities of the compound and the coformer in the solvent solution are each of a value sufficiently similar to form a cocrystal of the compound and the coformer as a single crystal phase.

According to yet another aspect of the disclosure, processes for scaled-up preparation of a cocrystal of a compound and a coformer are described, comprising combining the compound dissolved in a solvent solution with the coformer dissolved in the solvent solution, wherein the resulting cocrystal is crystallized from the solvent solution wherein the solubilities of the compound and the coformer in the solvent solution are each of a value sufficiently similar to form a cocrystal of the compound and the coformer as a single crystal phase.

According to a further aspect of the disclosure, processes for scaled-up preparation of a cocrystal of a compound and a coformer are described, comprising combining the compound dissolved in a solvent solution with the coformer added to form a slurry, wherein the resulting cocrystal is crystallized from the slurry.

In a still further aspect of the disclosure, a minoxidil: benzoic acid cocrystal is disclosed. The cocrystal may, in various embodiments, have, in its XRPD pattern, a peak at about 7.3°2Θ; at least two peaks at about 7.3°2Θ and 11.4°2Θ; or at least three peaks at about 7.3°2Θ, 11.4°2Θ, and 14.7°2Θ. In various embodiments, the cocrystal may have at least one peak chosen from 7.3°2Θ, 11.4°2Θ, 14.7°2Θ, 16.4°2Θ, 19.2°2Θ, 20.0°2Θ, 20.6°2Θ, 21.3°2Θ, 23.1°2Θ, or 26.5°2Θ. The cocrystal is believed to be a monohydrate.

DETAILED DESCRIPTION

The term "solvent solution" as used herein describes two or more solvents which are miscible with one another. Examples of miscible solvent solutions include, but are not limited to, isopropanol/water, acetone/water, acetonitrile/water, ethanol/water, methanol/water, butanol/water, tetrahydrofuran/heptane, isopropanol/heptane, acetone/heptane, ethyl acetate/heptane, methanol/tert-butyl methyl ether, or acetone/tert-butyl methyl ether.

The solvent solution may be composed of two or more solvents in different ratios. In one embodiment, the solvent solution is isopropanol/water and the ratio of isopropanol to water is 40:60 or 45:55, including between about 40% to about 50% isopropanol to water. In another embodiment, the solvent solution may be water/ethanol in a ratio of about 50:50, isopropanol/heptane in a ratio of about 50:50, ethyl acetate/heptane in a ratio of about 25:75, acetonitrile:water in a ratio of about 97:3, or isopropanol/water in a ratio of about 50:50.

In at least one further embodiment, a single solvent, in which the compound and conformer exhibit sufficiently similar solubilities, such as methylethylketone (MEK), may be used in place of a solvent system. In such embodiments, the use of the terms "solvent" and "solvent system" may be used interchangeably, without intending to alter the scope of the disclosure.

Once dissolved, the cocrystal may be prepared by precipitating the cocrystal from the solvent solution. Such precipitation may, for example, be a crystallization, and may occur by, for example, lowering the temperature of the solvent solution which contains the compound and coformer or removing the solvent solution via evaporation.

The term "approximately" as used herein in the context of the solubility of the compound in the solvent solution and the solubility of the coformer in the solvent solution means that the respective solubilities are sufficiently close so that congruent dissolution and congruent precipitation of the resulting cocrystal occurs.

Figure 1:
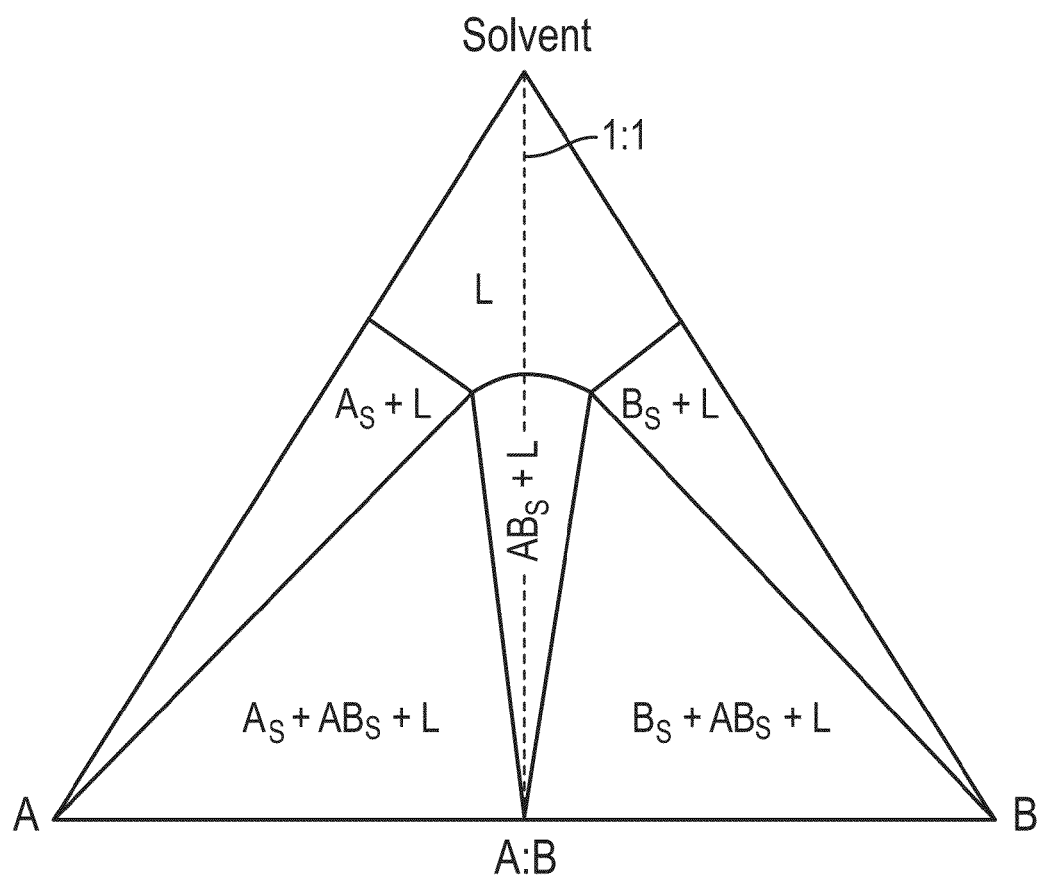
FIG. 1 is a phase diagram illustrating congruent dissolution.
Figure 2:
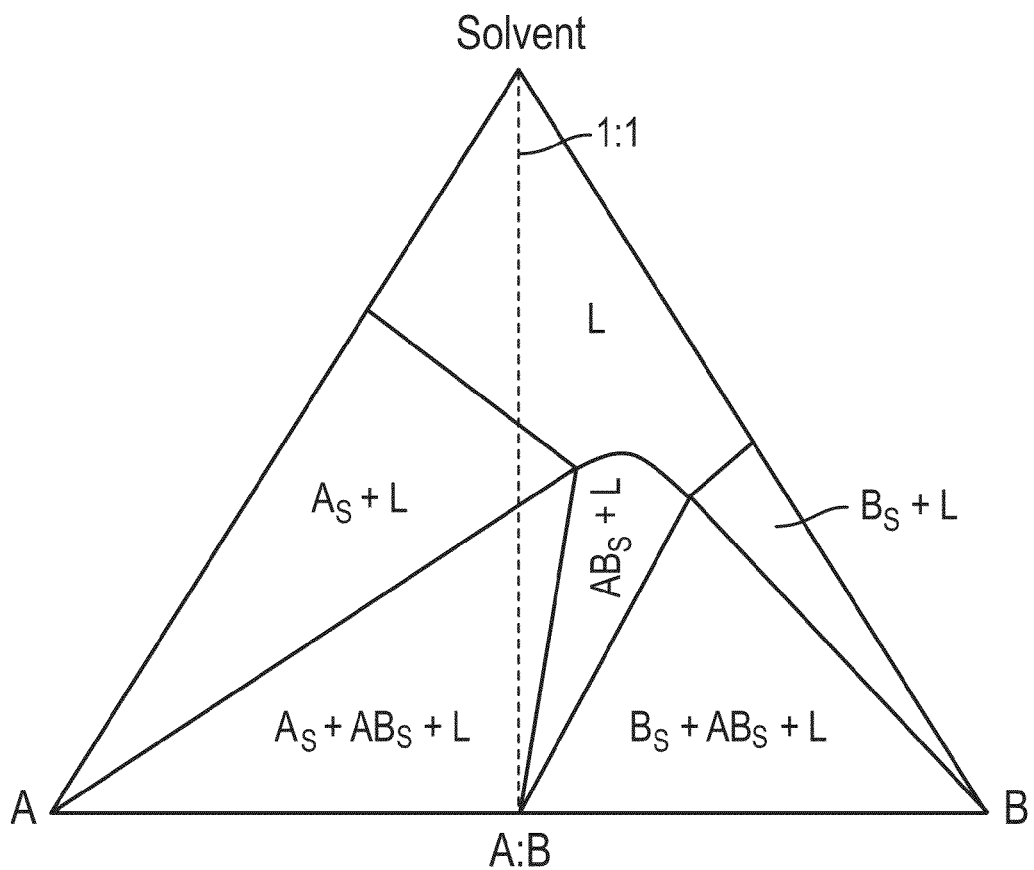
FIG. 2 is a phase diagram illustrating incongruent dissolution.

FIG. 1 and FIG. 2 provide illustrations of congruent dissolution and incongruent dissolution, respectively. In these figures, A and B refer to two components (compound and coformer), L refers to a liquid phase containing solvent and two components (compound and coformer), $A_s$ and $B_s$ refer to single phase solids containing one component (compound or coformer), while $AB_s$ refers to a two-component 1:1 cocrystal.

FIG. 1 illustrates congruent dissolution where the solubility of the two components is similar, resulting in an approximately symmetric phase diagram where the dashed line corresponding to a system containing a 1:1 ratio of each component crosses the region of the diagram where the cocrystal $AB_s$ can exist as a single solid phase. FIG. 1 demonstrates that for a solution of components A and B with a 1:1 ratio, the equilibrium solid phase is the single phase of the cocrystal $AB_s$ when the solubility of the two components is similar.

FIG. 2 illustrates incongruent dissolution, where the solubility of the two components is dissimilar, resulting in an asymmetric phase diagram where the dashed line corresponding to a system containing a 1:1 ratio of each component does not cross the region of the diagram where the cocrystal $AB_s$ can exist as a single solid phase. FIG. 2 demonstrates that for a solution of components A and B with a 1:1 ratio, the equilibrium solid phase is a mixture of one of the solid components ($A_s$ in the figure) and the cocrystal $AB_s$ when the solubility of the two components is dissimilar.

Overall, FIG. 1. and FIG. 2 together illustrate the fact that when preparing a 1:1 cocrystal using a 1:1 ratio of the two components, approximate matching of solubilities is essential to obtain the cocrystal as single phase solids upon filtration. Similar considerations exist when attempting cocrystals of other ratios of compound to coformer.

In at least one embodiment of the disclosure, the cocrystal is composed of a compound and a coformer wherein the cocrystal is a compound which is an active pharmaceutical ingredient or a nutraceutical and wherein the coformer is any acceptable coformer for use in humans. Examples of such acceptable coformers include compounds which appear on the GRAS (Generally Recognized as Safe) or EAFUS (Everything Added to Food in the United States) lists. Coformers may also include active pharmaceutical ingredients or nutraceuticals. One class of coformers useful according to various embodiments of the disclosure is a carboxylic acid and salts thereof. Other examples of coformers according to the processes of the disclosure include, but are not limited to, sugars, amino-acids and salts thereof, alkaloid and salts thereof, amines, sweeteners, and flavor agents.

The compound may be an acid or a base or neither. It may also be in the form of a salt. In one exemplary embodiment, the salt is a hydrochloride salt. Examples of compounds can be found, for example, in WO/2004/064762, which is herein incorporated by reference.

Crystallization of the cocrystals according to various embodiments of the disclosure may optionally be assisted by adding seeds to the crystallization vessel.

In one exemplary and non-limiting embodiment, caffeine is a coformer and pterostilbene is a compound. As shown in Table 1, pterostilbene was measured to have a solubility of 0.02 mg/mL in water whereas caffeine has a solubility of 18 mg/mL, nearly one thousand times higher. By comparison, pterostilbene's solubility was found to be 399 mg/ml in isopropyl alcohol, whereas the solubility of caffeine in isopropyl alcohol was found to be only 3 mg/mL. This large difference in solubility makes the scale-up of pterostilbene:caffeine challenging due to incongruent crystallization. Attempts to scale-up this cocrystal using a methyl-tert-butyl ether/heptane mixture, for example, have led to a physical mixture of cocrystal and caffeine.

TABLE 1

Solubility Estimates at Ambient Temperature

| Solvent | Pterostilbene (mg/mL) | Caffeine (mg/mL) | Cocrystal (mg/mL) |
|---|---|---|---|
| ACN | >203 | 21 | 34 |
| EtOAc | >201 | 7 | 17 |
| EtOH | 410 | 6 | 12 |
| Heptane | <2 | <1 | <1 |
| IPA | 399 | 3 | 9 |
| MEK | >200 | 8 | 18 |
| MTBE | >200 | <1 | 2 |
| Water | 0.02 | 18 | 0.5 |
| Water:IPA 55:45 | 22 | 38 | 28 |
| Water:IPA 60:40 | 22 | 37 | 20 |
| Water:IPA 70:30 | 2 | 39 | 4 |

As can be seen from Table 1, there is a general disparity between the solubility of pterostilbene and caffeine in a range of solvents. Pterostilbene tends to be more soluble in organic solvents than in water, whereas caffeine has a reverse tendency.

Figure 3:
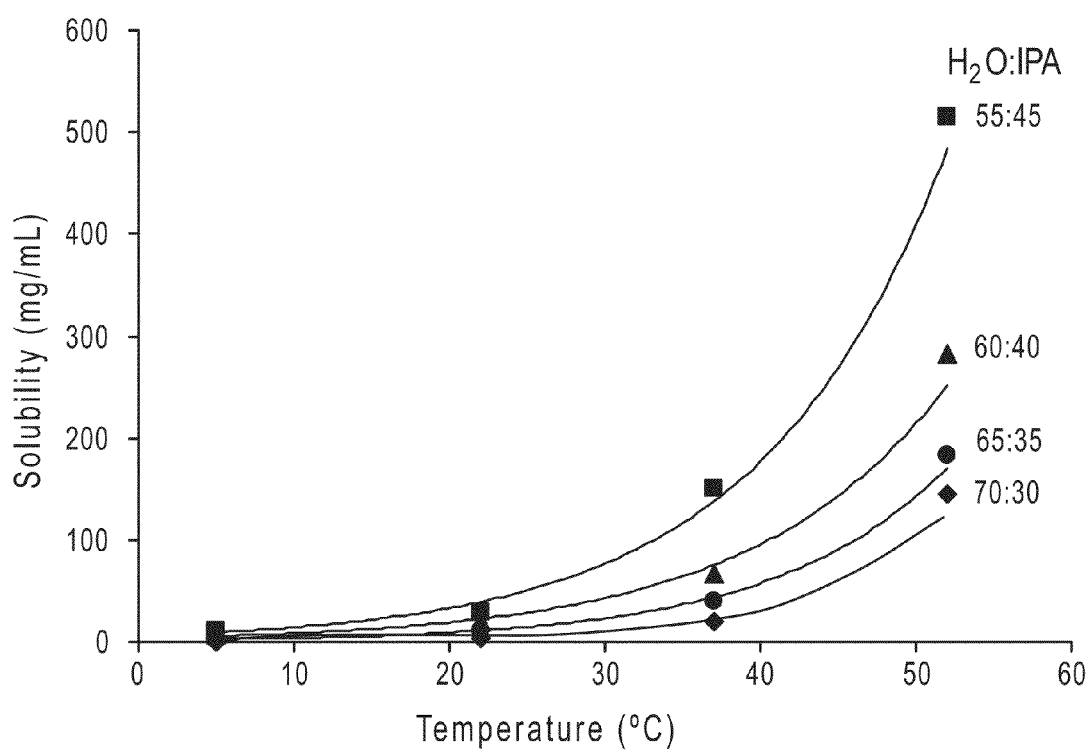
FIG. 3 is pterostilbene:caffeine cocrystal solubility/temperature graph under varying water:IPA solvent ratios.
Figure 4:
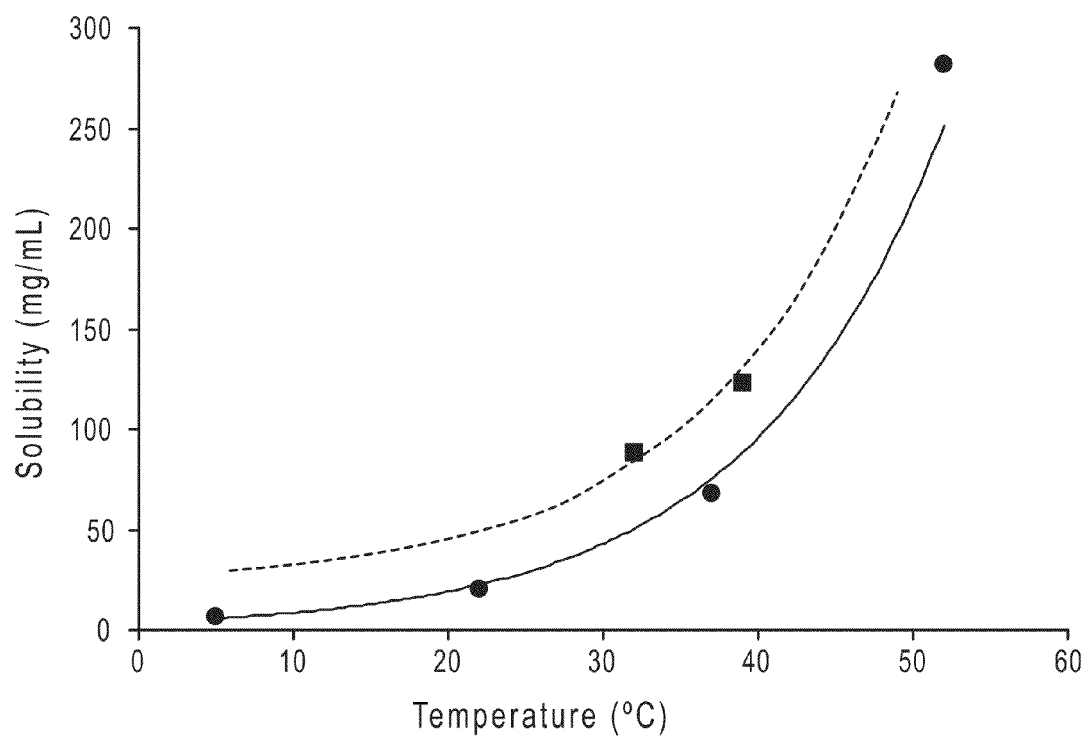
FIG. 4 is a solubility and metastable zone width graph at varying temperatures at a 60:40 water to IPA solvent ratio.
Figure 9:
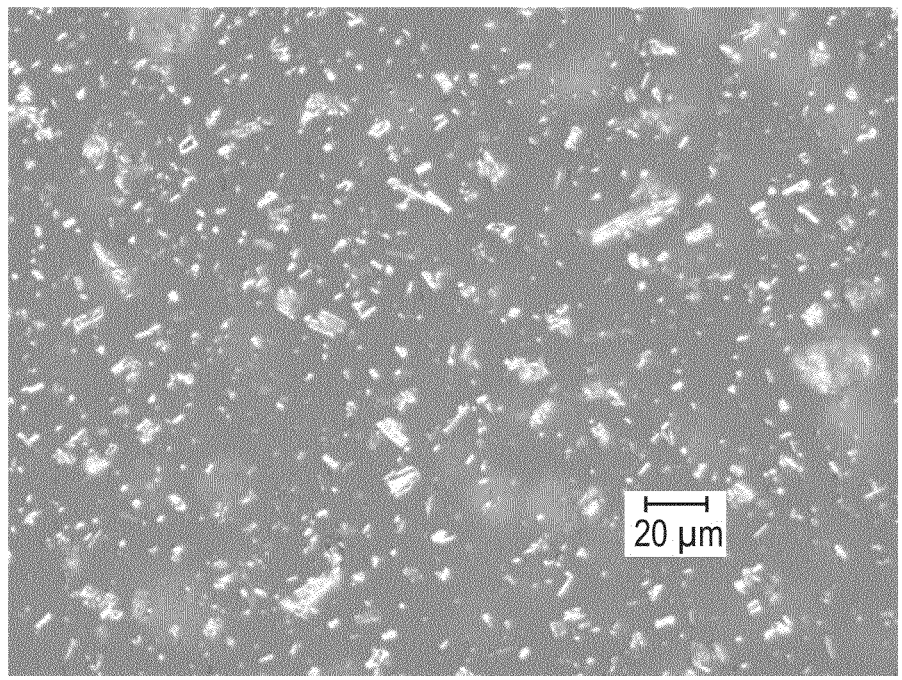
FIG. 9 is a microscopy image of an unseeded cooling experiment of the scale-up of pterostilbene:caffeine.

FIG. 3 illustrates the solubility of a cocrystal of pterostilbene:caffeine measured under different water:IPA conditions. Under such solvent conditions, sufficient dissolution from both components reduced the disparity between the solubility of each component, as for example, the 60:40 IPA:water mixture as seen in FIG. 4. In FIG. 4, the metastable zone width represented by the region between the solid and dashed lines was determined based on unseeded cooling at 0.2° C./min. Adequate seeding within this region using the desired form of a cocrystal allows control of solid form and particle size by avoiding spontaneous nucleation. FIG. 9 shows an image of a pterostilbene:caffeine cocrystals made without using seeds whereas in FIG. 10 seeds were used. The larger particles generated with seeds are advantageous for filtration and flow properties.

A 40:60 isopropanol to water mixture was used as a solvent solution and found to have comparable solubilities for both pterostilbene and caffeine at approximately 22 mg/L and 37 mg/mL, respectively. Increasing the water content to 70% and higher dropped the solubility of pterostilbene to approximately 2 mg/mL or less. In this solvent solution, the pterostilbene:caffeine 1:1 cocrystal had a solubility of approximately 18 mg/mL at room temperature.

In a further exemplary embodiment, the compound has a greater solubility in organic solvents than the coformer and the coformer has greater solubility in water than the compound. The solubility of the compound may be two times or more, three times or more, four times or more, five times or more, six times or more, seven times or more, eight times or more, nine times or more, ten times or greater, a hundred times or greater, or a thousand times or more greater than the solubility of the coformer in an organic solvent. The solubility of the coformer may be two times or more, three times or more, four times or more, five times or more, six times or more, seven times or more, eight times or more, nine times or more, ten times or greater, a hundred times or greater, or a thousand times or more greater than the solubility of the compound in water.

Table 2 illustrates the estimated solubilities of various compounds and coformers useful according to various embodiments of the disclosure, as well as their cocrystals, in various solvents and solvent solutions.

TABLE 2

Solubility Estimates at Ambient Temperature

| Cocrystal Compound 1: Coformer 2 (molar ratio) | Solvent system | Solubility Compound 1 (mg/mL) | Solubility Coformer 2 (mg/mL) | Solubility Cocrystal (mg/mL) |
|---|---|---|---|---|
| p-Coumaric acid: nicotinamide (1:1) | Methylethylketone | 70 | 22 | 10 |
| p-Coumaric acid: nicotinamide (2:1) | Acetonitrile: water 97:3 v/v | 28 | 42 | 22 |
| Pterostilbene: piperazine (1:1) | Water: ethanol 50:50 v/v | 54 | >324 | 10 |
| Minoxidil: benzoic acid (1:1) | Isopropanol: water 50:50 v/v | 27 | 26 | 14 |
| Progesterone: vanillic acid (1:1) | Isopropanol: heptane 50:50 v/v | 30 | 15 | 23 |
| Progesterone: cinnamic acid (1:1) | Ethyl acetate: heptane 25:75 v/v | 16 | 13 | 24 |

As illustrated in Table 2 above, and according to various non-limiting embodiments of the disclosure, the solubility of the compound in the solvent or solvent solution may be approximately equal to the solubility of the coformer in the solvent or solvent solution. In other exemplary and non-limiting embodiments, the solubility of the compound in the solvent or solvent solution is within a factor of 2 of the solubility of the coformer in the solvent or solvent solution. According to further non-limiting embodiments, the solubility of the compound in the solvent or solvent solution is within a factor of 10 of the solubility of the coformer in the solvent or solvent solution.

In Table 3, pterostilbene:caffeine cocrystals were prepared using the solvents indicated with the initial concentration of pterostilbene in the appropriate solvent provided. Upon addition of caffeine and a suitable anti-solvent, the resulting cocrystal is prepared, with a yield as provided in Table 3.

TABLE 3

Experimental Slurry Conditions

| Solvent | Initial Pterostilbene Concentration (mg/mL) | Yield |
|---|---|---|
| EtOH | 80 | 65% |
| | 100 | 71% |
| | 120 | 74% |
| | 150 | 79% |
| MTBE | 100 | 81% |

TABLE 3-continued

Experimental Slurry Conditions

| Solvent | Initial Pterostilbene Concentration (mg/mL) | Yield |
|---|---|---|
| MTBE addition of heptane MTBE:heptane 1:1 | 100 | 91%[a] |
| MTBE addition of heptane MTBE:heptane 1:1 wash with water | 100 | 86% |

[a] Residual caffeine detected

Figure 8:
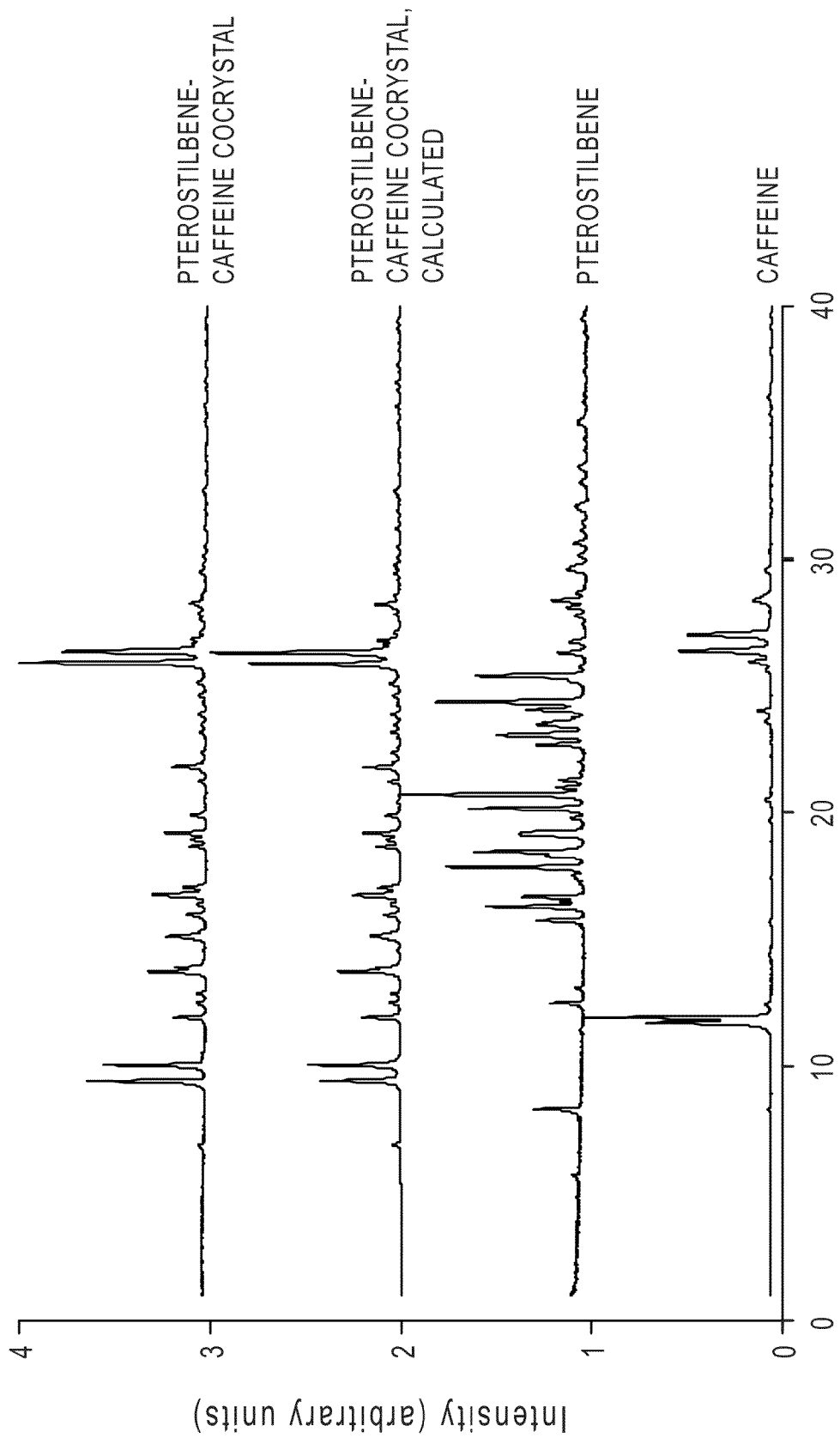
FIG. 8 is an overlay of the x-ray powder diffraction (XRPD) pattern of pterostilbene:caffeine cocrystal obtained upon scale up as described in Example 4, a calculated pattern based on single crystal data for pterostilbene:caffeine cocrystal Form I reported previously (N. Schultheiss, S. Bethune, and J.-O. Henck, Nutraceutical cocrystals: utilizing pterostilbene as a cocrystal former, Crystal Engineering Communications, 2010, 12, 2436-2442), and XRPD patterns of pterostilbene and caffeine forms used for the cocrystallization experiments.

Table 4 illustrates varying water:IPA ratios, seeding conditions, starting concentrations, and yields for the scale-up of pterostilbene:caffeine cocrystals. FIG. 8 shows an overlay of the x-ray powder diffraction pattern of a material obtained at large scale by a cooling, seeded method, compared to the calculated x-ray powder pattern from single crystal data published for pterostilbene:cocrystal Form I (N. Schultheiss, S. Bethune, and J.-O. Henck, Nutraceutical cocrystals: utilizing pterostilbene as a cocrystal former, Crystal Engineering Communications, 2010, 12, 2436-2442), and XRPD patterns of pterostilbene and caffeine forms used for the cocrystallization experiments.

TABLE 4

Cooling process experimental conditions

| Water:IPA Ratio (v/v) | Scale[a] | Conditions[b] | Starting concentration | Yield |
|---|---|---|---|---|
| 55:45 | 7.2 g | unseeded | 90 mg/mL (11 vol) | 81% |
| 60:40 | 7.2 g | unseeded | 90 mg/mL (11 vol) | 73% |
| 60:40 | 7.2 g | seeded | 90 mg/mL (11 vol) | 81% |
| 60:40 | 5.6 g | unseeded | 70 mg/mL (14 vol) | 77% |
| 60:40 | 5.6 g | seeded | 70 mg/mL (14 vol) | 83% |
| 60:40 | 56 g | seeded | 70 mg/mL (14 vol) | 90% |

[a] Mass refers to pterostilbene
[b] Cooling crystallizations with a cooling rate of 0.2° C./min In a further embodiment of the disclosure, processes for the scaled-up preparation of a cocrystal of a compound and a coformer are described comprising combining the compound dissolved in a solvent solution with the coformer added to form a slurry and wherein the resulting cocrystal is crystallized from the slurry. Such crystallization may also be done in the presence of an anti-solvent such as a hydrocarbon.

Figure 5:
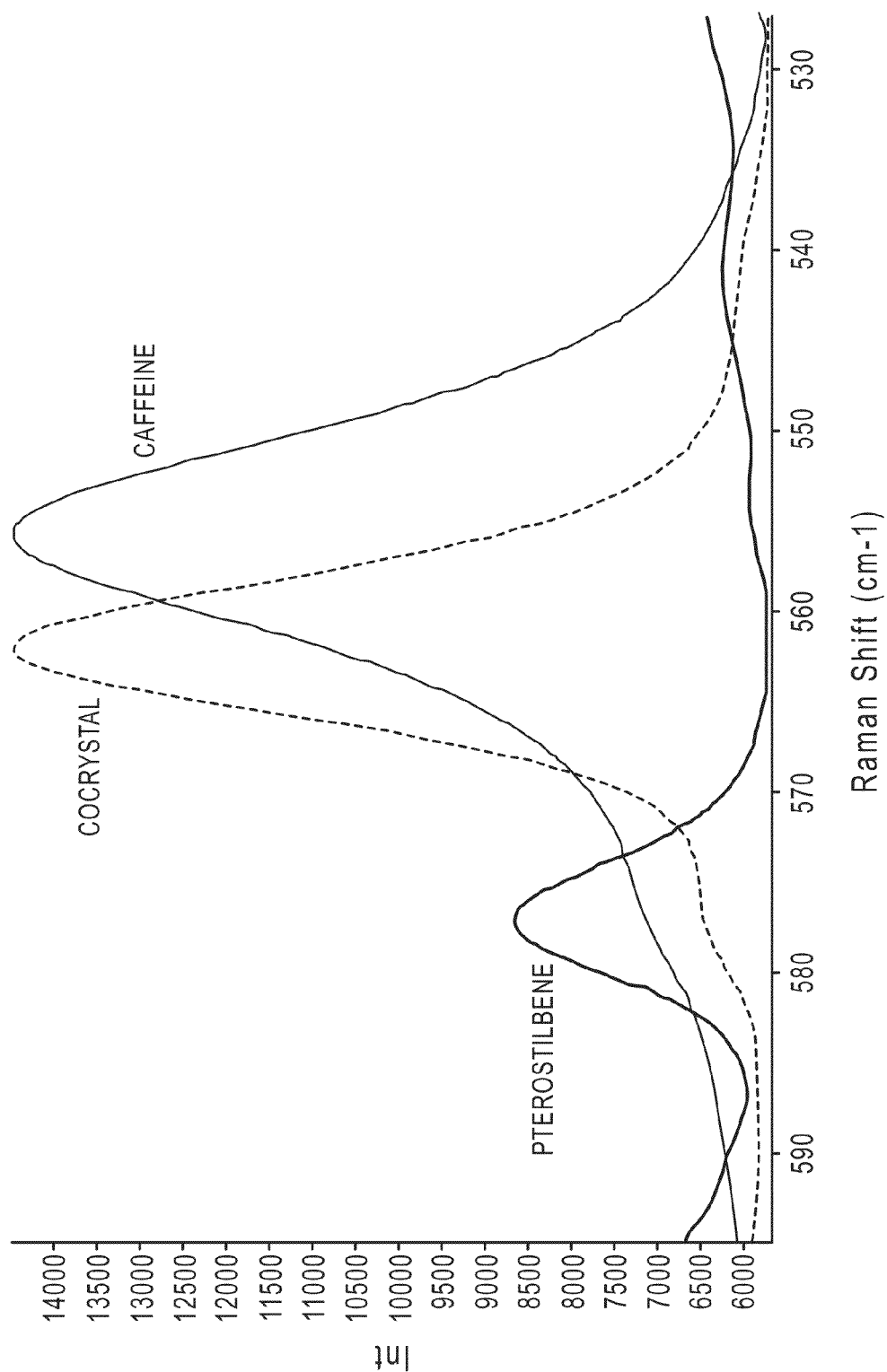
FIG. 5 is an overlay of Raman spectra of pterostilbene: caffeine cocrystal (red), pterostilbene and caffeine in the 565-540 cm$^{-1}$ region.
Figure 6:
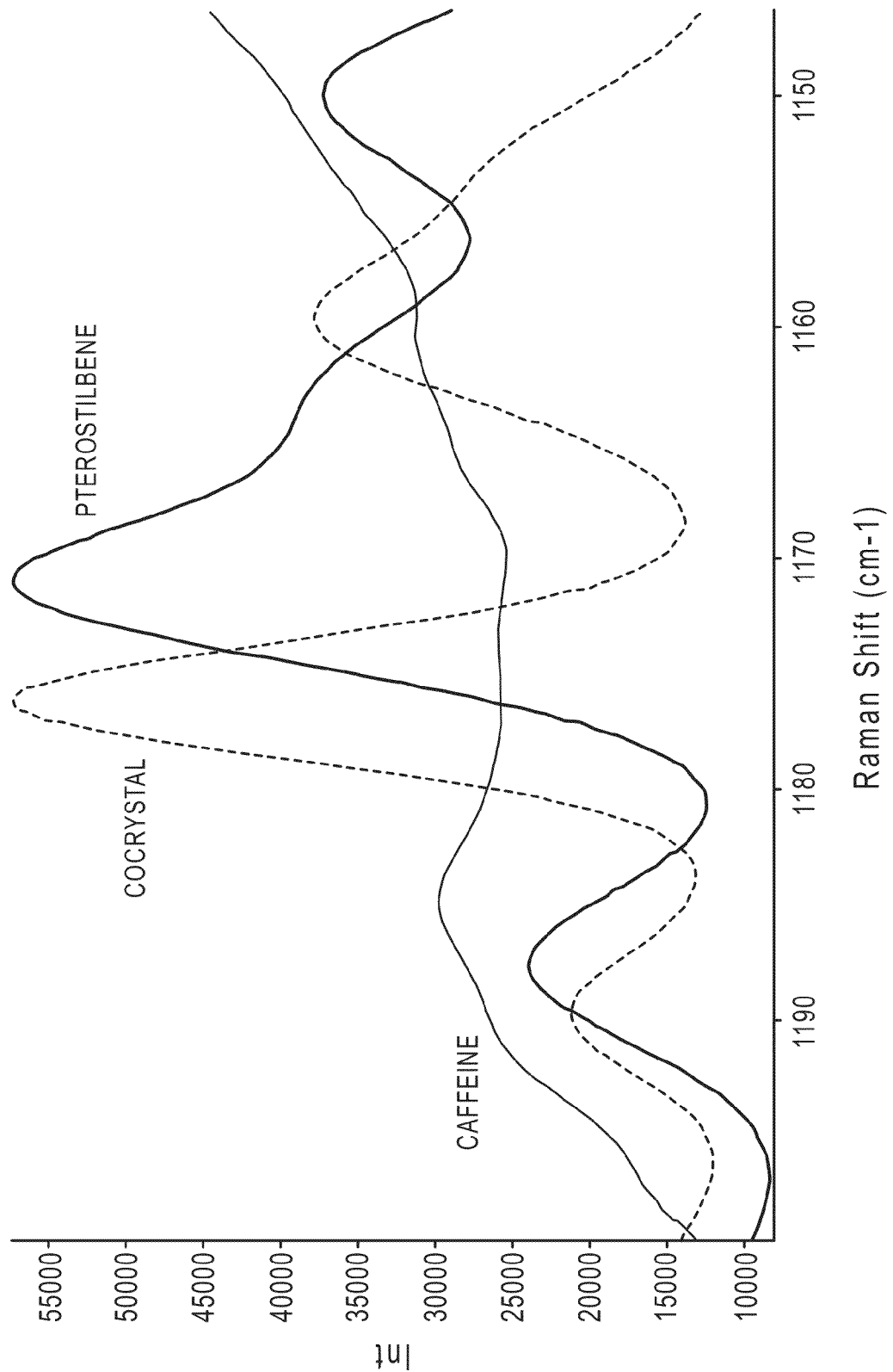
FIG. 6 is an overlay of Raman spectra of pterostilbene: caffeine cocrystal (red), pterostilbene, and caffeine in the 1185-1165 cm$^{-1}$ region.
Figure 7:
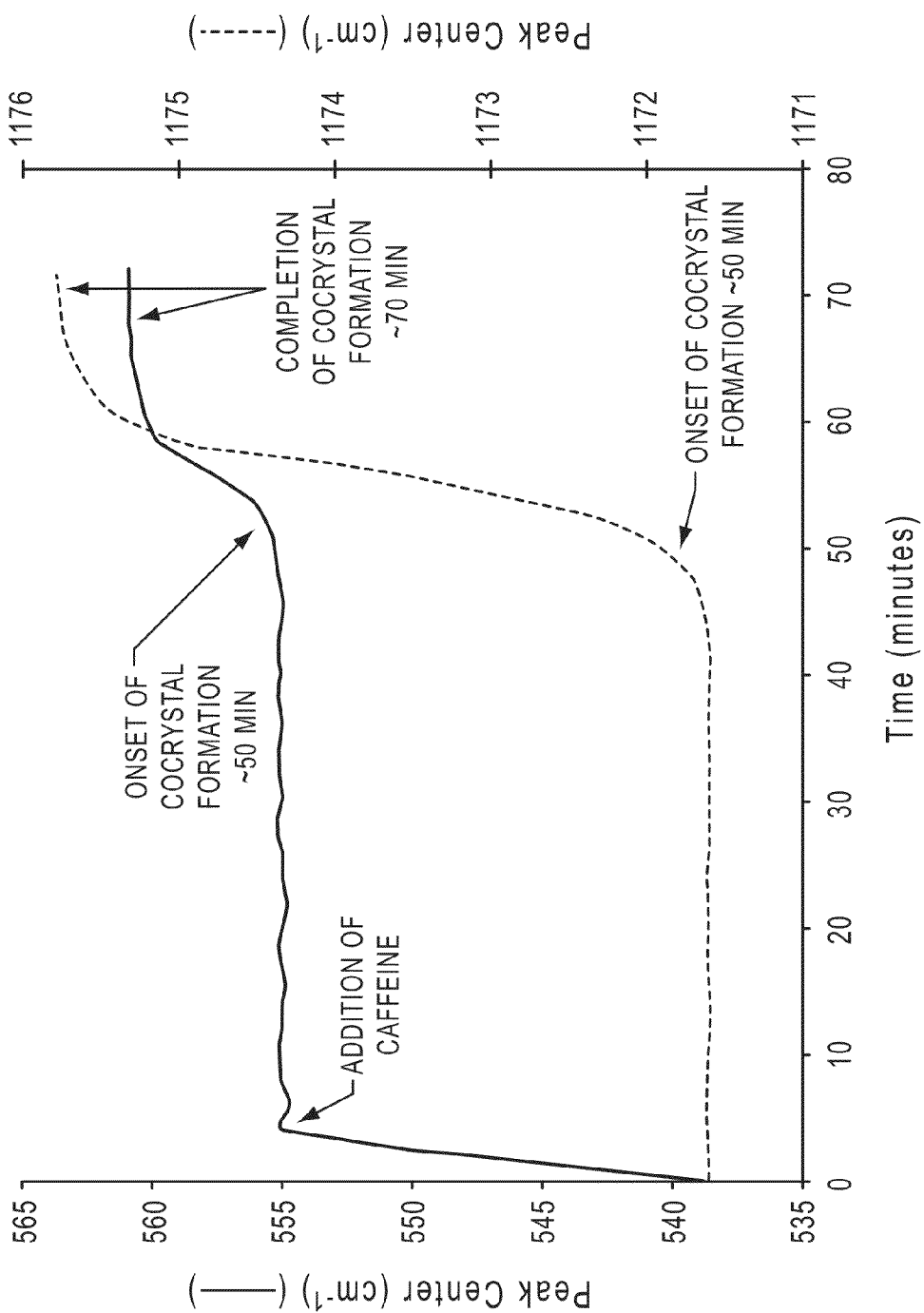
FIG. 7 is a time-resolved graph for the formation of a pterostilbene:caffeine cocrystal based on peak center in the 565-540 cm$^{-1}$ region and based on peak center in the 1185-1165 cm$^{-1}$ region.

In one embodiment, a slurry for the preparation of a pterostilbene:caffeine cocrystal is described. An exemplary preparation is described in Example 8. In this and other embodiments, Raman spectroscopy, including Raman microscopy, may be used to monitor the formation of the cocrystal from the compound and the coformer. FIG. 5, for example, shows specificity between pterostilbene, caffeine, and the pterostilbene:caffeine cocrystal in one region of the Raman spectrum. FIG. 6 shows specificity in another region. By monitoring a slurry process with Raman microscopy in situ, one is, therefore, able to monitor the formation of a cocrystal and differentiate it from the corresponding compound and coformer. FIG. 7 shows such real-time monitoring of the formation of the pterostilbene:caffeine cocrystal using Raman spectroscopy.

By "specificity" what is meant is sufficient separation between selected Raman peaks in Raman spectra collected on the compound, the coformer and the cocrystal of interest so that one of ordinary skill in the art can readily determine which signal corresponds to which of the three of compound, coformer, or cocrystal. In the case of pterostilbene:caffeine cocrystal, this separation is visually apparent since the corresponding peak maxima do not overlap.

Many different analytical techniques are available to detect and analyze the cocrystals made according to the processes disclosed herein. A number of solid-state analytical techniques that can be used to provide information about solid-state structure and may be used to analyze cocrystals made according to the disclosure, including, by way of example only, single crystal x-ray diffraction, x-ray powder diffraction (XRPD), solid-state $^{13}C$ NMR, Raman spectroscopy, and thermal techniques such as Differential Scanning Calorimetry (DSC), melting point, and hot stage microscopy.

EXAMPLES

Prophetic Example 1

No Seeding

A reactor vessel is charged with a solid compound and a solid coformer and a solvent system comprising of a miscible water-solvent solution. The solubility of each of the component is within a factor of ten in the solution. The system is heated until dissolution and then is cooled to form a suspension. The suspension is filtered and vacuum dried, yielding a cocrystal of the compound and the coformer at gram scale quantities.

Prophetic Example 2

With Seeding

The procedures of Example 1 are carried out with the addition of seed crystals of the cocrystal of the compound to the reactor vessel containing a solution of the compound and coformer prior to spontaneous nucleation.

Methods

Solubility estimations were performed gravimetrically or via slow incremental addition of solvent to weighted amounts of solids. Slurry experiments and small scale cooling experiments were performed in vials or small round bottom flasks which were magnetically stirred. Multi-gram cooling experiments were performed using a 100 mL or 1 L round bottom controlled laboratory reactor (Radleys Lara CLR) equipped with a Mettler Toledo turbidity probe, a Teflon anchor impeller, Julabo temperature control unit, and a temperature probe for monitoring the reactor temperature throughout the experiments. The Lara Technologies software (v. 2.0.0.49) tracked circulator temperature, vessel temperature, stir rate, and turbidity. Slurry experiments were typically conducted by preparing a solution of pterostilbene in solvent and subsequent addition of coformer solids. Cooling experiments were conducted by mixing pterostilbene and caffeine and then adding the aqueous isopropanol mixture. The system was heated at a rate of 2 degrees per minute to 60 or 70 degrees followed by cooling to 5 degrees with a cooling rate of 0.2 degrees per minute (all Celsius).

Raman measurements of the slurry experiments were performed using a Kaiser dispersive Raman RXN3 with 785 nm excitation.

X-ray powder diffraction (XRPD) data were taken either on a PANalytical X'Pert Pro or a INEL XRG-3000 diffractometer using Cu Kα radiation (λ=1.54059 Å).

Polarized light microscopy was collected using a Leica DMLP microscope equipped with a Spot Insight Color Camera. Crossed polarizers with first order red compensators and Kohler illumination were used.

Differential scanning calorimetry (DSC) analyses were performed using a TA Instruments 2920 differential scanning calorimeter. The samples were heated from 25° C. to 300° C. at a rate of 10° C./min.

Thermogravimetric (TG) analyses were performed using a TA Instruments 2950 thermogravimetric analyzer. The sample was heated from room temperature to 350° C. at a rate of 10° C./min.

Solution proton NMR ($^1$H NMR) spectra were acquired at ambient temperature with a Varian$^{UNITY}$ INOVA-400 spectrometer at a $^1$H Larmor frequency of 399.796 MHz. The spectrum was acquired with a $^1$H pulse width of 9.0 μs, a 5.00 second acquisition time, a 2.50 second delay between scans, a spectral width of 6400 Hz with 64000 data points.

Coulometric Karl Fischer (KF) analysis for water determination was performed using a Mettler Toledo DL39 KF titrator.

Example 3

100 mL Reactor Pterostilbene:Caffeine Scale-Up Cocrystal Process—with Seeding

A 100 mL reactor vessel was charged with solid pterostilbene (7.20 g; 28.1 mmol) and caffeine (5.46 g, 28.1 mmol), and 80 ml of water: isopropanol 60:40 solvent mixture. The pterostilbene concentration was 90 mg/mL. The system was heated from 40 to 70° C. for 15 minutes or with heating rate 2° C./min, hold at 70° C. for 10 minutes, and then cooled from 70° C. to 60° C. with cooling rate 0.2° C./min. The system was seeded with 145 mg (~2 wt %) of pterostilbene: caffeine 1:1 cocrystal, Form I as a slurry with concentration of 90 mg/mL in water:isopropanol 60:40 while holding the temperature for 30 minutes at 60° C. The system was cooled from 60 to 5° C. with cooling rate of 0.2° C./min. The solution became cloudy at 57° C. The system was allowed to cool to 5° C. with cooling rate of 0.2° C./min. The resulting suspension was stirred at 5° C. for 17.5 hours. One volume wet cake of water: isopropanol 60:40 was added into the reactor. The system was slurried at 5° for 40 minutes. After the discharge of the suspension, the reactor was washed with one volume wet cake (19 mL) of chilled water: isopropanol 60:40 solvent mixture. The suspension was filtered to dry land using a Buchner funnel and a filter paper and washed with the washing from the reactor filtered to completion. The solid was vacuum dried at approximately 40° C. for 25.5 hours yielding 12.66 g of pterostilbene:caffeine 1:1 cocrystal, Form I (81% yield).

Structure was confirmed by comparison of XRPD data with calculated XRPD data from single crystal x-ray data available for the cocrystal.

Example 4

1 L Reactor Pterostilbene:Caffeine Scale-Up Cocrystal Process—with Seeding

Figure 10:
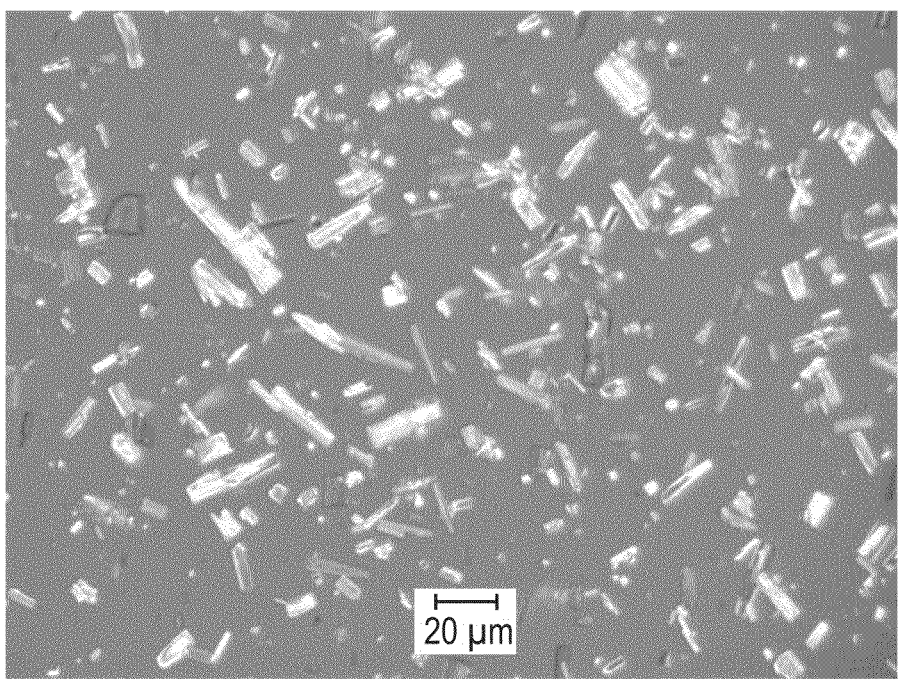
FIG. 10 is a microscopy image of a seeded cooling experiment of the scale-up of pterostilbene:caffeine.

A 1 L reactor vessel was charged with solid pterostilbene (56.0 g; 0.2185 mol) and caffeine (42.43 g, 0.2185 mol), and 800 ml of water: isopropanol 60:40 solvent mixture. The pterostilbene concentration was 70 mg/mL. The system was heated from 30 to 60° C. for 15 minutes or with 2° C./min heating rate, hold at 60° C. for 30 minutes, and then cooled from 60° C. to 42° C. with cooling rate of 0.2° C./min. The system was seeded with 1.12 g (~2 wt %) of pterostilbene: caffeine 1:1 cocrystal, Form I as a slurry with concentration of 110 mg/mL in water:isopropanol 60:40 while holding the temperature for 1 hour at 42° C. The system was cooled from 42 to 5° C. with cooling rate of 0.2° C./min. The resulting suspension was stirred at 5° C. for 13.5 hours. After the discharge of the suspension, the reactor was washed with one volume wet cake (250 mL) of chilled water: isopropanol 80:20 solvent mixture. The suspension was filtered to dry land using a Buchner funnel and a filter paper and washed with the washing from the reactor and filtered to completion. The solid was vacuum dried at approximately 40° C. for 20 hours yielding 89.13 g of pterostilbene: caffeine 1:1 cocrystal, Form I (90% yield). A micrograph of the pterostilbene:caffeine cocrystal thus formed is illustrated in FIG. 10.

Example 5

Pterostilbene:Caffeine Scale-Up Cocrystal Process—without Seeding

A 100 mL reactor vessel was charged with solid pterostilbene (7.2 g; 28.1 mmol) and caffeine (5.457 g, 28.1 mmol), and 80 ml of water: isopropanol 60:40 solvent mixture. The pterostilbene concentration was 90 mg/mL. The system was heated from 30 to 70° C. for 20 minutes or with heating rate 2° C./min, held at 70° C. for 10 minutes, and then cooled from 70° C. to 5° C. with cooling rate 0.2° C./min. The resulting suspension was stirred at 5° C. for 18 hours. After the discharge of the suspension, the reactor was washed twice with one volume wet cake (2×19 mL) of chilled water: isopropanol 60:40 solvent mixture. The suspension was filtered to dry land using a Buchner funnel and a filter paper and washed with the washings from the reactor also to dry land. The final wash of the filter cake was performed using one cake of wash solvent system (chilled water: isopropanol 60:40) and filtered to completion. The solid was vacuum dried at 40° C. yielding 9.202 g of pterostilbene: caffeine 1:1 cocrystal, Form I (73% yield). A micrograph of the pterostilbene:caffeine cocrystal thus formed is illustrated in FIG. 9.

Prophetic Example 6

Slurry Process

A solid compound is dissolved in a solvent to form a solution. A solid coformer is added to the solution. The suspension is stirred until the formation of cocrystal is complete. In some cases, aliquots of an anti-solvent may subsequently be added to the solution. Solids formed in the solution are filtered and dried. The solid is a cocrystal of the compound and the coformer.

Example 7

Preparation of Pterostilbene:Caffeine Cocrystal by a Slurry Process

Solid pterostilbene (1.5 g, 5.86 mmol) was dissolved in 15 mL of t-butyl methyl ether (MTBE). The concentration of pterostilbene was calculated to be 100 mg/mL. Caffeine (1.14 g, 5.86 mmol) was added to the solution and the resulting slurry was allowed to stir at ambient temperature for 24 hours. Then aliquots of heptane (total 15 mL) were added with stirring to reach MTBE:heptane ratio 1:1. The system was allowed to stir at ambient temperature for 4 hours. The solid was collected by vacuum filtration on paper filter, washed 2×5 mL of heptane, and air-dried under reduced pressure for 10 minutes. The solid was transferred in an Erlenmeyer flask and 13 mL of water were added. The resulting slurry was allowed to stir at ambient temperature for 0.5 hour. The solid was isolated by vacuum filtration on a paper filter, washed 2×5 mL of water and then air-dried under reduced pressure for 40 minutes. The solid was vacuum dried at approximately 40° C. for 3 days yielding 2.26 g of pterostilbene: caffeine 1:1 cocrystal, Form I (86% yield).

Example 8

Preparation of Pterostilbene:Piperazine 2:1 Cocrystal with Seeding

Figure 11:
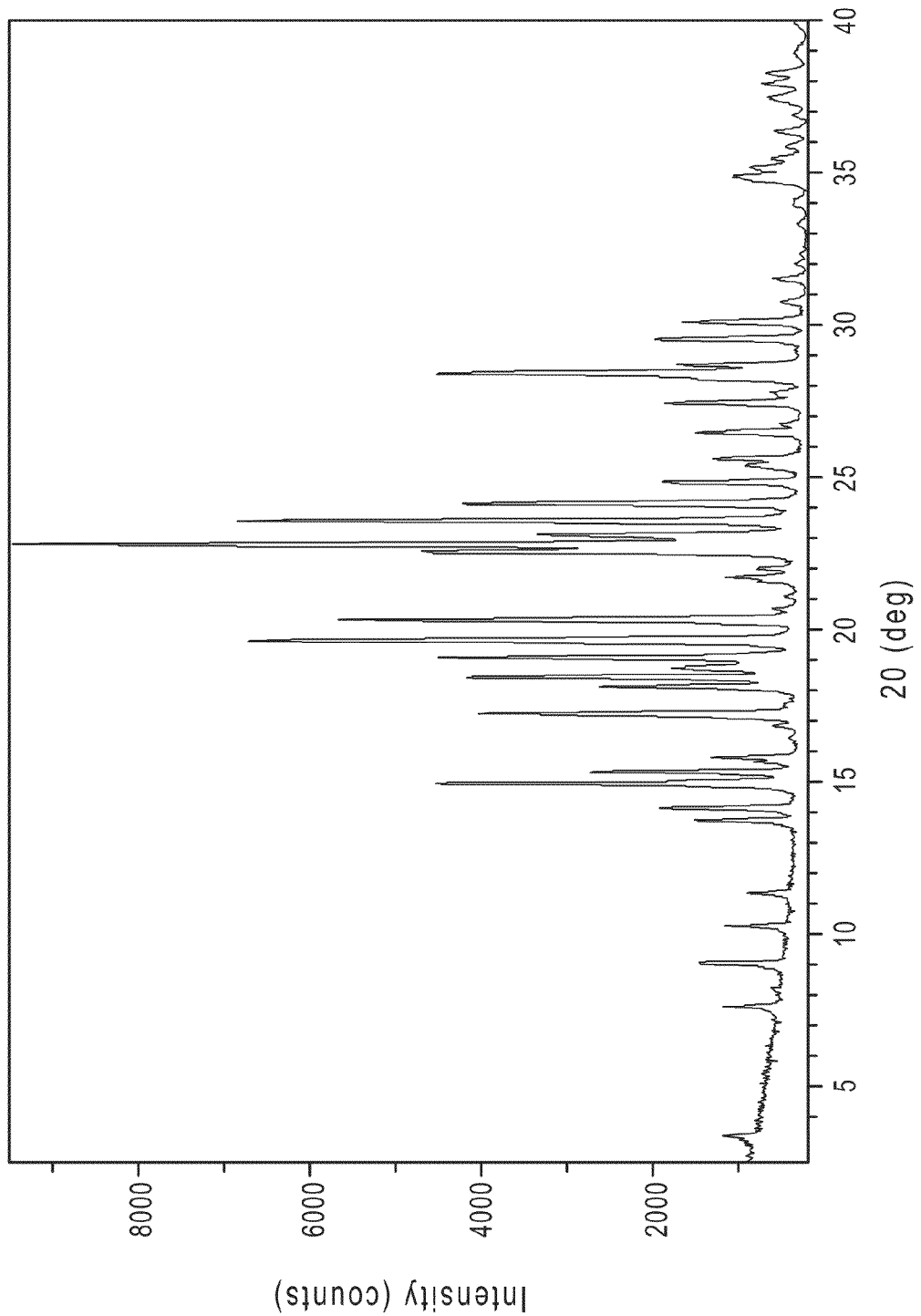
FIG. 11 is the XRPD pattern of scaled up pterostilbine: piperazine 2:1 cocrystal obtained in Example 8.

An Erlenmeyer flask was charged with solid pterostilbene (1.0038 g) and piperazine (0.1688 mg), and 12.5 mL of an ethanol:water 50:50 solvent mixture. The system was heated to 59° C. with stirring, resulting in a slightly turbid yellow solution. The sample was then cooled at a rate of 0.2° C./min to 51° C. The system was seeded with 4 wt % pterostilbene: piperazine 2:1 cocrystals, which dissolved upon addition. The system was further cooled at a rate of 0.2° C./min to 48° C. The system was again seeded with 3 wt % pterostilbene: piperazine 2:1 cocrystals, which did not dissolve upon addition. The system was stirred at 48° C. for 30 minutes and then cooled to 25° C. at a cooling rate of 0.2° C./min. Upon reaching 25° C., the sample was placed in a cold room and allowed to stir at subambient temperature for 19 hours. The solid was then collected by vacuum filtration on a paper filter, washed three times with 3.0 mL (3×3.0 mL) of chilled ethanol:water 50:50 solvent mixture. The solid was vacuum dried at 41° C. for 23 hours, yielding 0.9753 g of pterostilbene: piperazine 2:1 cocrystal (76% yield). The structure of the pterostilbene:piperazine 2:1 cocrystal was confirmed by XRPD, as illustrated in FIG. 11.

Example 9

Preparation of Progesterone:Vanillic Acid 1:1 Cocrystal with Seeding

Figure 12:
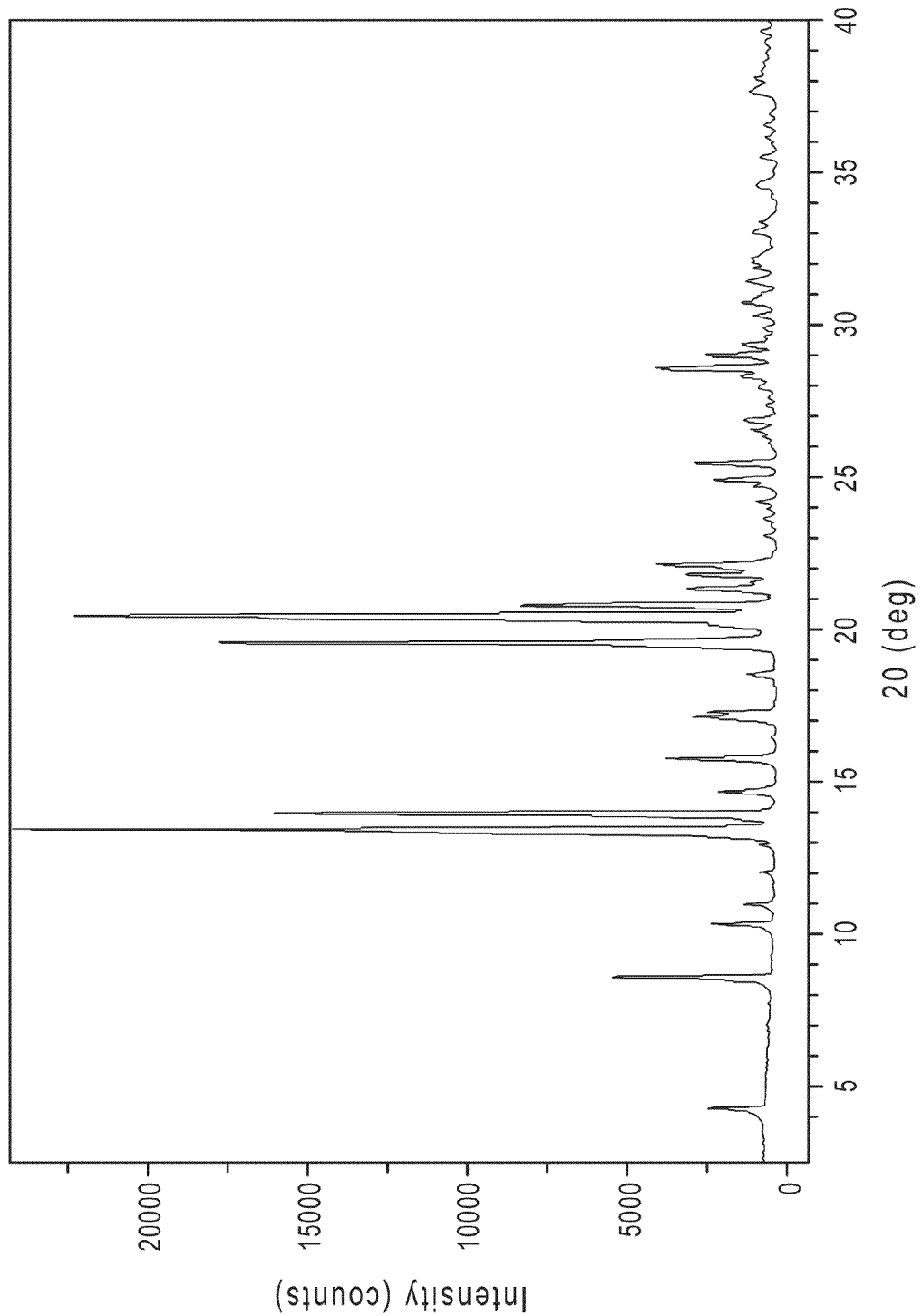
FIG. 12 is the XRPD pattern of scaled up progesterone: vanillic acid 1:1 cocrystal obtained in Example 9.

A 100 mL reactor was charged with progesterone (8.45 g) and vanillic acid (4.55 g), and 85 mL of an isopropanol: heptane 50:50 solvent mixture. The system was heated from room temperature to about 75° C. over a period of approximately one hour. The resulting solution was cooled to approximately 60° C. over a period of 30 minutes. The system was seeded with 78.8 mg progesterone:vanillic acid 1:1 cocrystals, added as a suspension in 2 mL of heptane. The system was held for one hour before cooling to 10° C. over a period of five hours. The system was stirred overnight at 10° C. and the solids were subsequently isolated by vacuum filtration on a paper filter. The solids were dried in a vacuum oven at ambient temperature for one day, yielding 10.8 g of progesterone:vanillic acid 1:1 cocrystal (83% yield). The structure of the progesterone:vanillic acid 1:1 cocrystal was confirmed by XRPD, as illustrated in FIG. 12.

Example 10

Preparation of Progesterone:Cinnamic Acid ~1:1 Cocrystal with Seeding

Figure 13:
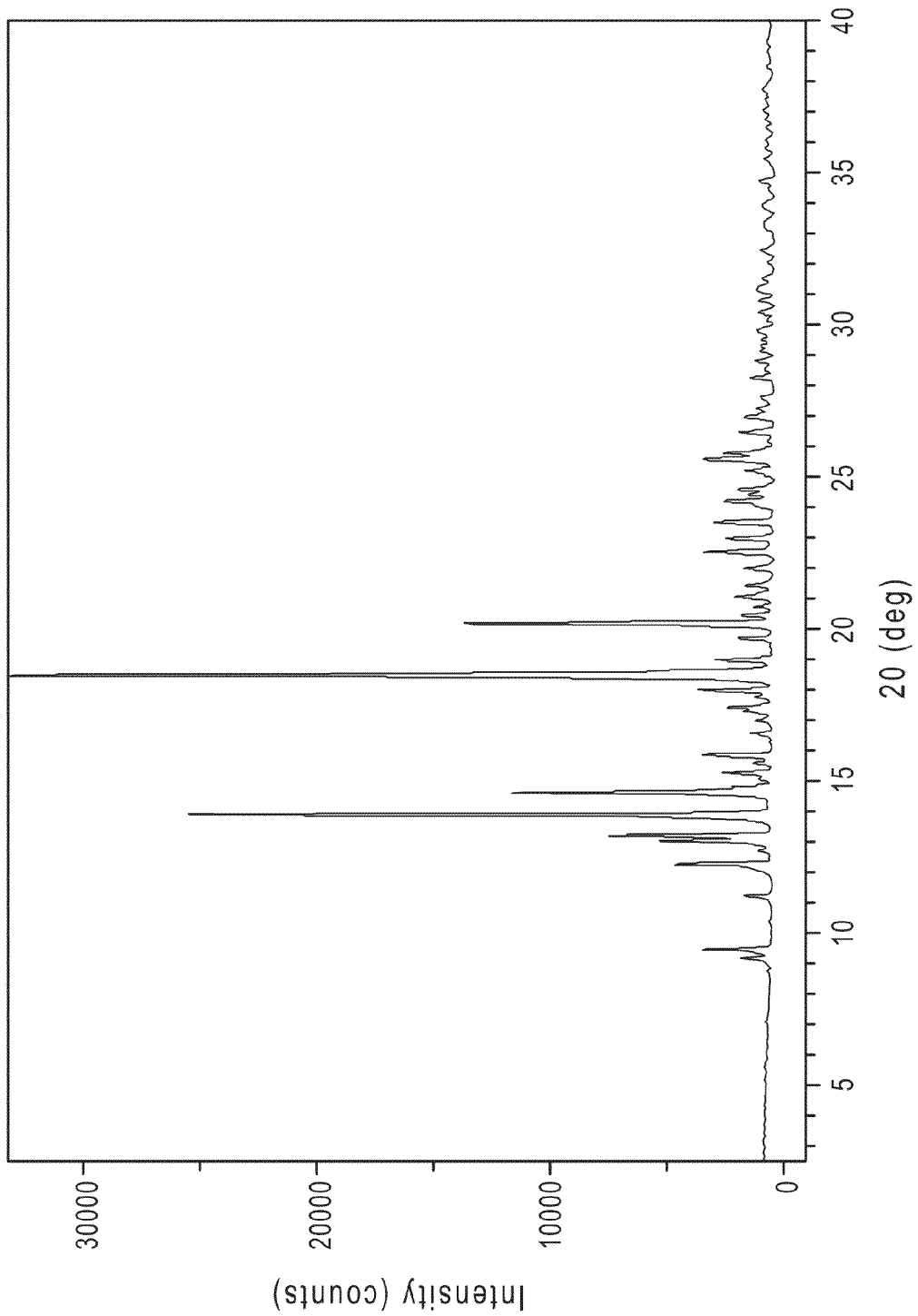
FIG. 13 is the XRPD pattern of scaled up progesterone: cinnamic acid ~1:1 cocrystal obtained in Example 10.

A 100 mL reactor was charged with progesterone (9.338 g) and cinnamic acid (4.416 g), and 75 mL of an ethyl acetate: heptane 25:75 solvent mixture. The system was heated from room temperature to about 65° C. and held at this temperature until a clear solution was obtained. The resulting solution was cooled to 55° C. over a period of 15 minutes. The system was seeded with 9.7 mg progesterone:cinnamic acid ~1:1 cocrystals, added as a suspension in 1 mL of heptane. The system was cooled from 55° C. to 50° C. over a period of 75 minutes and then cooled to 15° C. over a period of 12 hours. The solids were isolated by vacuum filtration on a paper filter and dried in a vacuum oven at ambient temperature for approximately one day, yielding 10.2 g of progesterone:cinnamic acid ~1:1 cocrystal (74% yield). The structure of the progesterone: cinnamic acid ~1:1 cocrystal was confirmed by XRPD, as illustrated in FIG. 13.

Example 11

Preparation of P-Coumaric Acid:Nicotinamide 1:1 Cocrystal with Seeding

Figure 14:
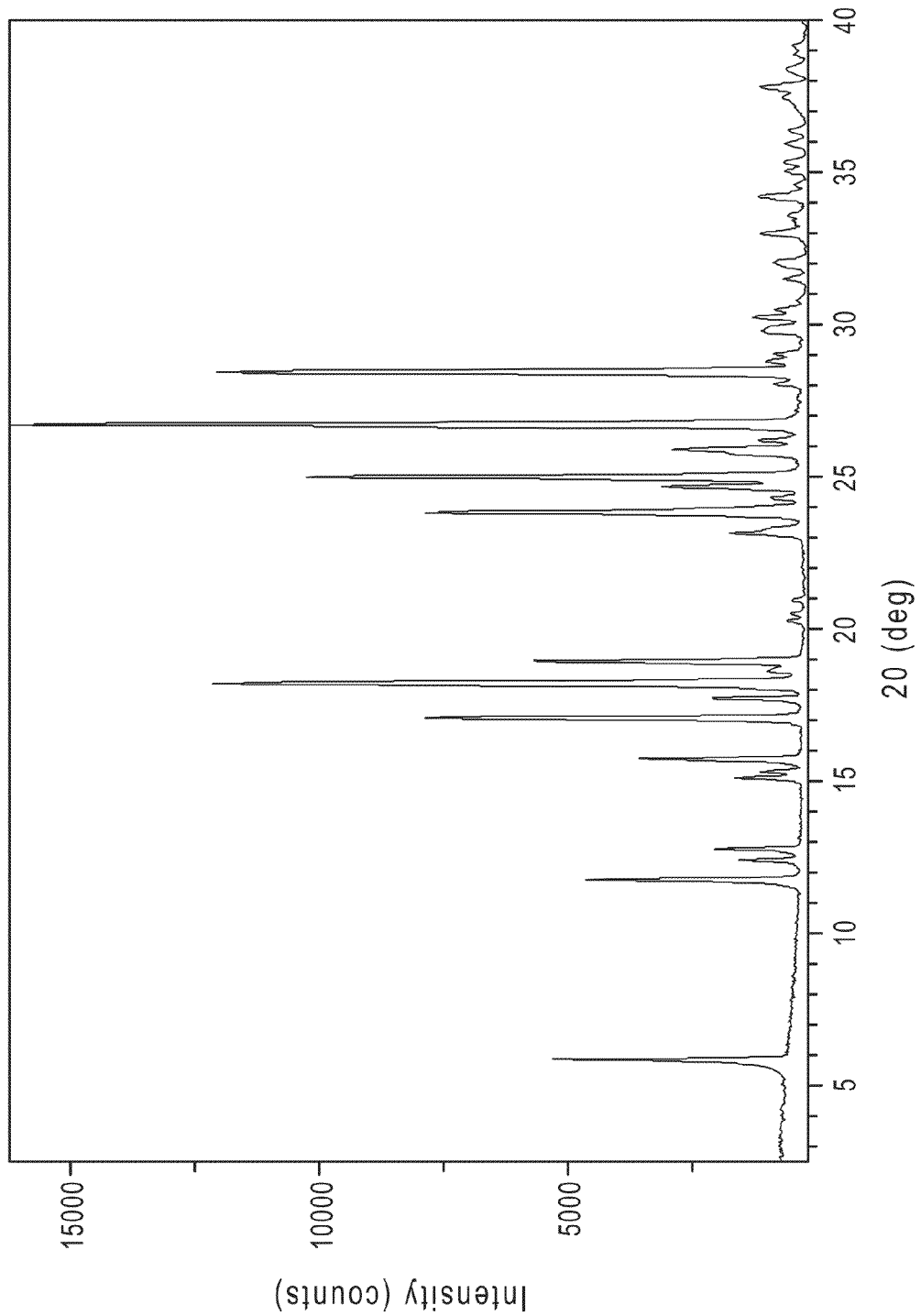
FIG. 14 is the XRPD pattern of scaled up p-coumaric acid:nicotinamide 1:1 cocrystal obtained in Example 11.

A 100 mL reactor was charged with a 1:1 molar ratio of solid p-coumaric acid (6.5211 g) and nicotinamide (4.7544 g), and 100 mL of methylethylketone (MEK) with overhead stirring. The system was heated to 78° C. with stirring, and an additional 10 mL of MEK was added to the reactor, resulting in a clear solution. The system was cooled to 69° C. over a period of 50 minutes. The system was seeded with 0.1358 g p-coumaric acid:nicotinamide 1:1 cocrystals, added as a slurry in 3 mL of MEK. The system was held for one hour at 69° C. before cooling to 10° C. over a period of 295 minutes. The system was held overnight at 10° C. and the solids were subsequently isolated by vacuum filtration on a paper filter. The solids were dried in a vacuum oven at ambient temperature for one day, yielding a p-coumaric acid:nicotinamide 1:1 cocrystal (81% yield). The structure of the p-coumaric acid: nicotinamide 1:1 cocrystal was confirmed by XRPD, as illustrated in FIG. 14.
\

Example 12

Preparation of P-Coumaric Acid:Nicotinamide 2:1 Cocrystal with Seeding

Figure 15:
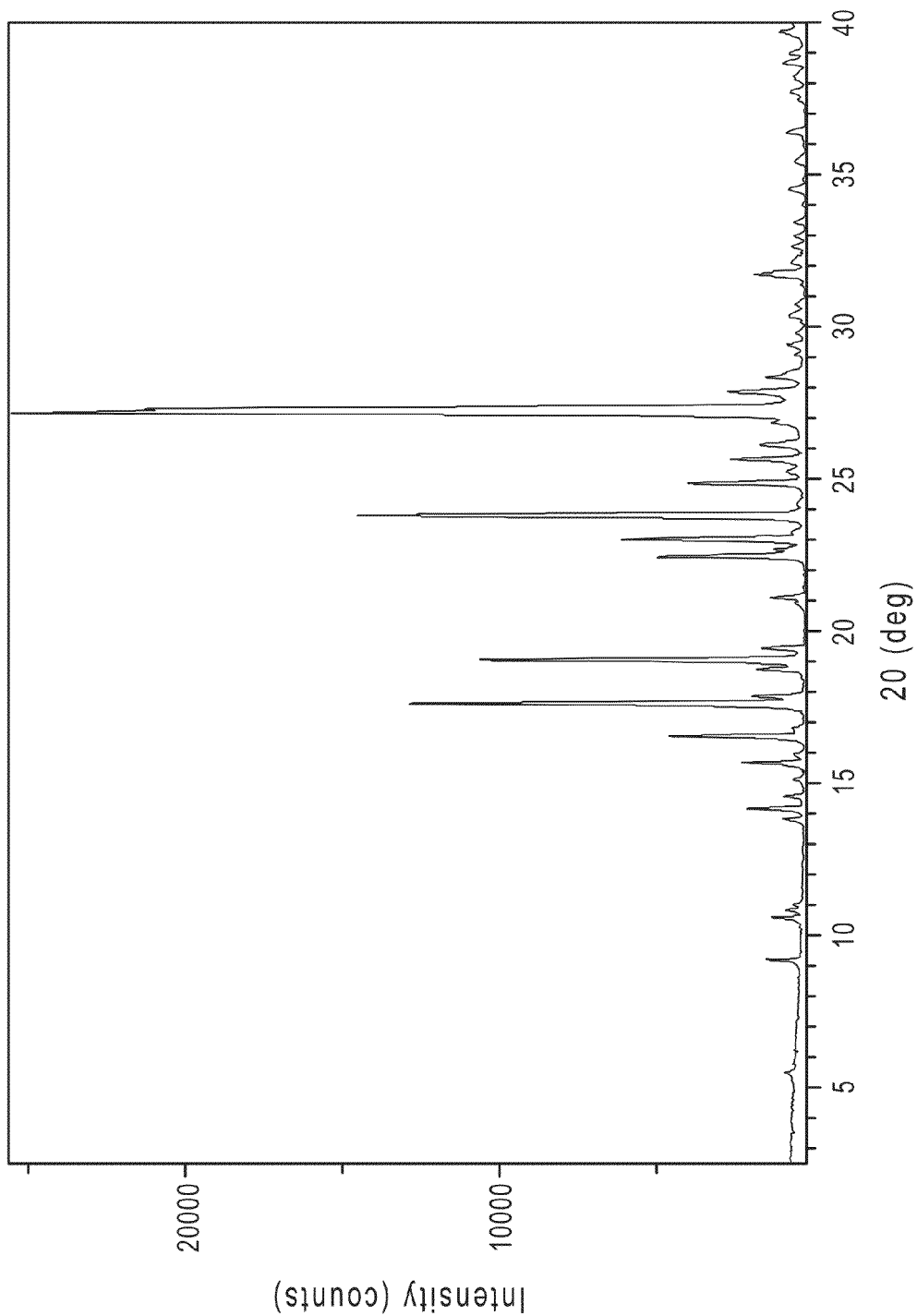
FIG. 15 is the XRPD pattern of scaled up p-coumaric: nicotinamide 2:1 cocrystal obtained in Example 12.

A 100 mL reactor was charged with solid p-coumaric acid (7.6892 g) and nicotinamide (2.8060 g), and 100 mL of acetonitrile (ACN):water 97:3 solvent mixture with overhead stirring. The system was heated to 76° C. over a period of 30 minutes with stirring, and an additional 10 mL of ACN:water 97:3 solvent mixture was added to the reactor. The system was cooled to 70° C. at a rate of 0.2° C./min. The system was seeded with 0.1544 g p-coumaric acid:nicotinamide 2:1 cocrystals, added as a slurry in 6 mL of ACN:water 97:3 solvent mixture. The system was held for 30 minutes at 70° C. before cooling to 10° C. at a rate of 0.2° C./min. The system was held overnight at 10° C. and the solids were subsequently isolated by vacuum filtration on a paper filter. The solids were dried in a vacuum oven at ambient temperature for one day, yielding a p-coumaric acid:nicotinamide 2:1 cocrystal (73% yield). The structure of the p-coumaric acid:nicotinamide 2:1 cocrystal was confirmed by XRPD, as illustrated in FIG. 15.

Example 13

Preparation of Minoxidil:Benzoic Acid 1:1 Monohydrate Cocrystal without Seeding

A 250 mL round bottom flask was charged with solid minoxidil (21.209 g), 85 mL isopropanol, and 85 mL water.

The system was heated from room temperature to approximately 75° C. with stirring, until the solids dissolved. A 50 mL round bottom flask was charged with benzoic acid (12.421 g), 21 mL of isopropanol, and 21 mL of water. The system was heated from room temperature to approximately 75° C. with stirring, until the solids dissolved. The benzoic acid solution was added to the minoxidil solution and the resulting system was cooled to approximately 69° C. and held at this temperature for one hour. Precipitation of white solids was observed. The system was slowly cooled to room temperature before being placed in a refrigerator with stirring for about one day. Solids were collected by vacuum filtration and dried under vacuum at room temperature, yielding 31.8 g of minoxidil:benzoic acid 1:1 monohydrate cocrystal (90% yield).

Figure 16:
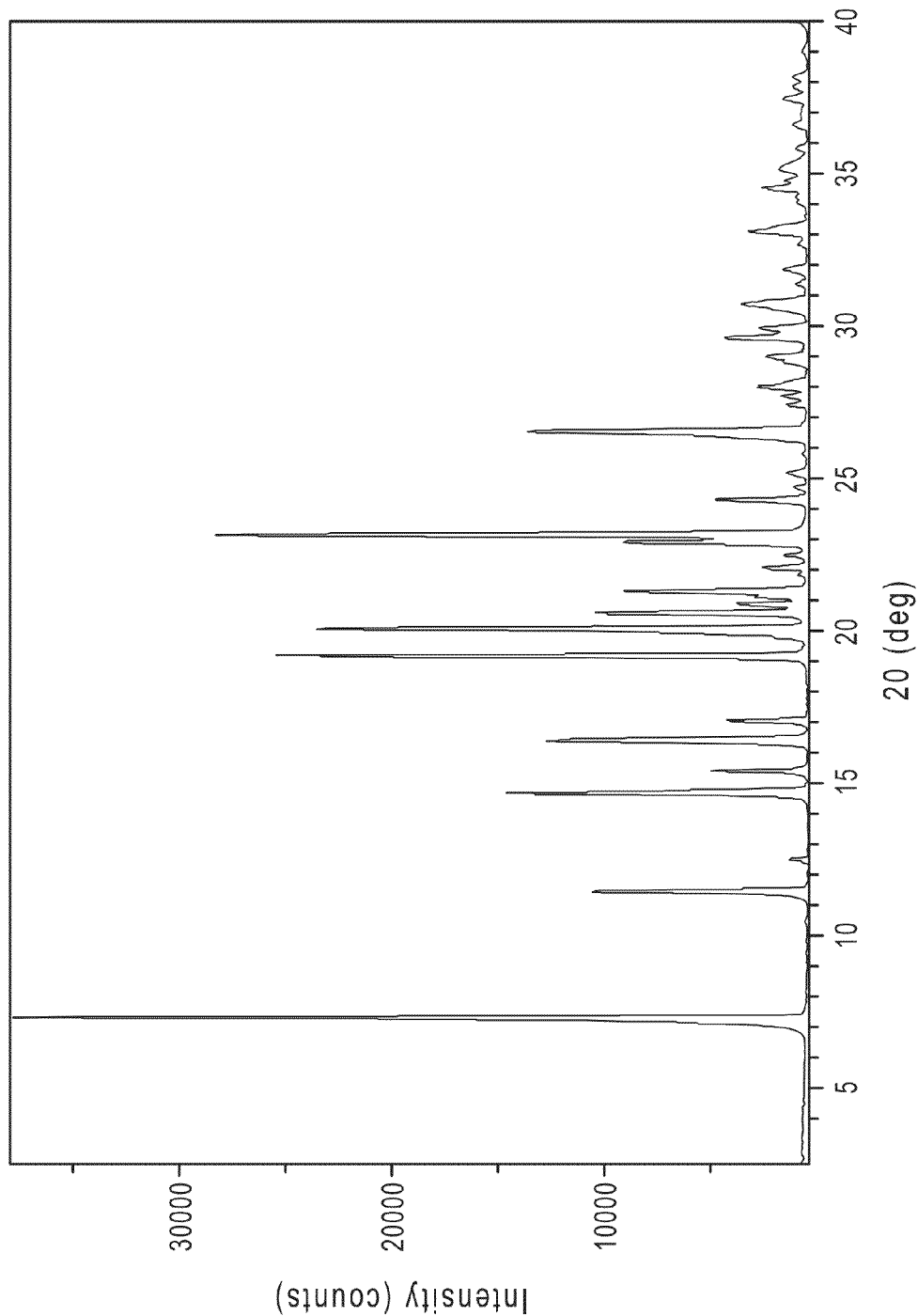
FIG. 16 is the XRPD pattern of scaled up minoxidil:benzoic acid 1:1 monohydrate cocrystal obtained in Example 13.
Figure 17:
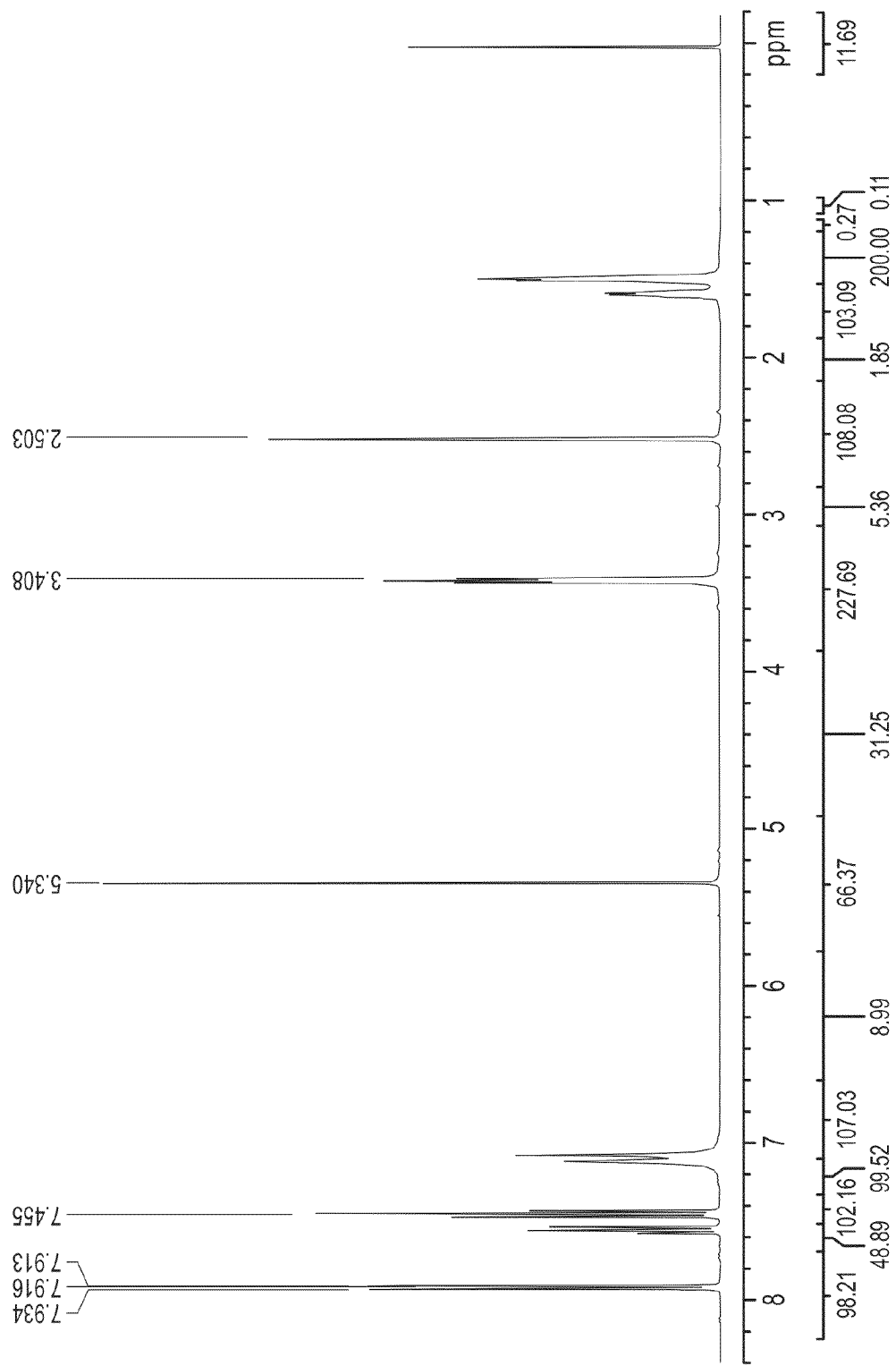
FIG. 17 illustrates the solution proton NMR ($^1$H NMR) analysis of scaled up minoxidil:benzoic acid 1:1 monohydrate cocrystal obtained in Example 13.
Figure 18:
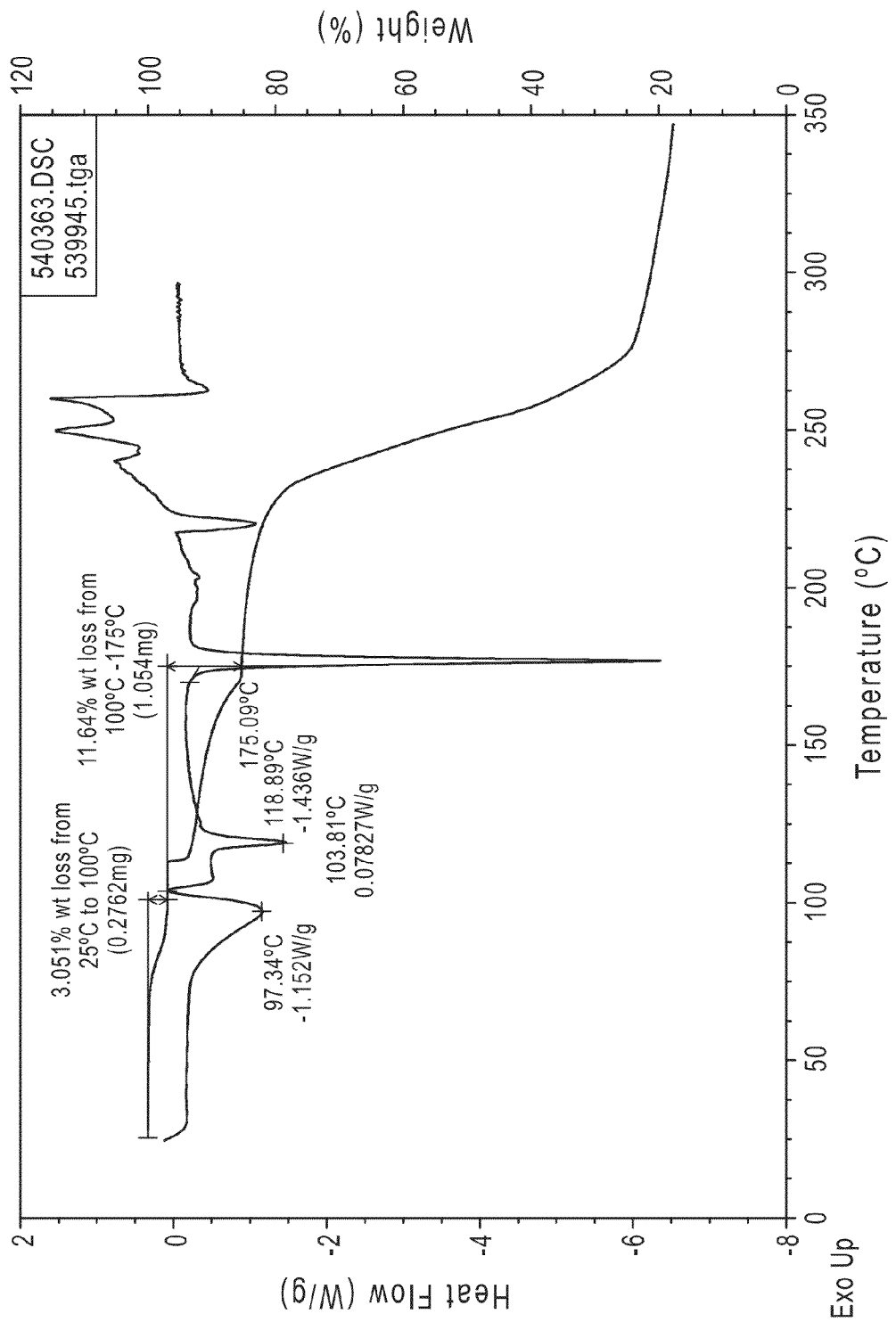
FIG. 18 illustrates the differential scanning calorimetry (DSC) and thermogravimetric (TG) analyses of scaled up minoxidil:benzoic acid 1:1 monohydrate cocrystal obtained in Example 13.

The structure of the minoxidil:benzoic acid 1:1 monohydrate cocrystal was confirmed by XRPD, as illustrated in FIG. 16. Solution proton NMR data confirmed the presence of minoxidil and benzoic acid in a 1:1 ratio, as illustrated in FIG. 17. Differential scanning calorimetry (DSC) and thermogravimetric (TG) analyses were performed on the minoxidil:benzoic acid cocrystal, the results of which are illustrated in FIG. 18. A Karl Fischer analysis of the cocrystal yielded approximately 4.9 wt % water, which is approximately consistent with the presence of 1 mole of water per mole of cocrystal (theoretical value is approximately 5.2 wt % water).

Tables 5 and 6 below describes in more detail the peaks observed in the XRPD pattern depicted in FIG. 16. Specifically, Table 5 lists the observed peaks and Table 6 lists the representative peaks.

TABLE 5

XRPD Observed Peaks for Minoxidil:Benzoic Acid 1:1 Monohydrate

| °2θ | d space (Å) | Intensity (%) |
| --- | --- | --- |
| 7.29 ± 0.20 | 12.130 ± 0.342 | 100 |
| 11.42 ± 0.20 | 7.752 ± 0.138 | 28 |
| 12.47 ± 0.20 | 7.099 ± 0.115 | 3 |
| 14.66 ± 0.20 | 6.044 ± 0.083 | 39 |
| 15.38 ± 0.20 | 5.763 ± 0.075 | 13 |
| 16.38 ± 0.20 | 5.412 ± 0.066 | 34 |
| 17.03 ± 0.20 | 5.206 ± 0.061 | 11 |
| 19.15 ± 0.20 | 4.634 ± 0.048 | 67 |
| 20.02 ± 0.20 | 4.435 ± 0.044 | 64 |
| 20.56 ± 0.20 | 4.321 ± 0.042 | 28 |
| 20.84 ± 0.20 | 4.262 ± 0.041 | 10 |
| 21.09 ± 0.20 | 4.212 ± 0.040 | 8 |
| 21.28 ± 0.20 | 4.176 ± 0.039 | 24 |
| 21.81 ± 0.20 | 4.075 ± 0.037 | 2 |
| 22.04 ± 0.20 | 4.032 ± 0.036 | 7 |
| 22.44 ± 0.20 | 3.961 ± 0.035 | 4 |
| 22.86 ± 0.20 | 3.890 ± 0.034 | 24 |
| 23.11 ± 0.20 | 3.848 ± 0.033 | 76 |
| 24.27 ± 0.20 | 3.668 ± 0.030 | 13 |
| 24.67 ± 0.20 | 3.609 ± 0.029 | 3 |
| 25.14 ± 0.20 | 3.543 ± 0.028 | 4 |
| 25.79 ± 0.20 | 3.455 ± 0.027 | 2 |
| 26.51 ± 0.20 | 3.363 ± 0.025 | 36 |
| 27.39 ± 0.20 | 3.256 ± 0.023 | 4 |
| 27.66 ± 0.20 | 3.225 ± 0.023 | 4 |
| 27.96 ± 0.20 | 3.191 ± 0.023 | 7 |
| 28.78 ± 0.20 | 3.102 ± 0.021 | 4 |
| 28.95 ± 0.20 | 3.085 ± 0.021 | 6 |
| 29.58 ± 0.20 | 3.020 ± 0.020 | 11 |
| 29.88 ± 0.20 | 2.990 ± 0.020 | 7 |

TABLE 6

XRPD Representative Peaks for Minoxidil:Benzoic Acid 1:1 Monohydrate

| °2θ | d space (Å) | Intensity (%) |
| --- | --- | --- |
| 7.29 ± 0.20 | 12.130 ± 0.342 | 100 |
| 11.42 ± 0.20 | 7.752 ± 0.138 | 28 |
| 14.66 ± 0.20 | 6.044 ± 0.083 | 39 |
| 16.38 ± 0.20 | 5.412 ± 0.066 | 34 |
| 19.15 ± 0.20 | 4.634 ± 0.048 | 67 |
| 20.02 ± 0.20 | 4.435 ± 0.044 | 64 |
| 20.56 ± 0.20 | 4.321 ± 0.042 | 28 |
| 21.28 ± 0.20 | 4.176 ± 0.039 | 24 |
| 23.11 ± 0.20 | 3.848 ± 0.033 | 76 |
| 26.51 ± 0.20 | 3.363 ± 0.025 | 36 |

Example 14

Preparation of Minoxidil:Benzoic Acid 1:1 Monohydrate Cocrystal (Single Crystal Preparation)

A vial was charged with 30 mg of minoxidil:benzoic acid 1:1 monohydrate cocrystal, 2 mL of acetonitrile, and 1 mL of water. The sample was sonicated until a clear solution was obtained. The vial was covered with paraffin and five holes were paced into the film to allow for the slow evaporation of the solvent mixture. Solids were observed in the vial after approximately 8 days. The sample was capped and the crystals were harvested for the single crystal analysis, described in more detail below.

Example 15

Single Crystal Structure Determination of Minoxidil:Benzoic Acid 1:1 Monohydrate Crystal Experimental Data Collection A colorless chunk of $C_{16}H_{23}N_5O_4$ having approximate dimensions of 0.20×0.18×0.14 mm, was mounted on a fiber in random orientation. Preliminary examination and data collection were performed with Cu $K_\alpha$ radiation ($\lambda$=1.54184 Å) on a Rigaku Rapid II diffractometer equipped with confocal optics. Refinements were performed using SHELX97[i].

Cell constants and an orientation matrix for data collection were obtained from least-squares refinement using the setting angles of 15819 reflections in the range 3°<θ<66°. The refined mosaicity from CrystalClear is 0.66° indicating moderate crystal quality. The space group was determined by the program XPREP. From the systematic presence of the following conditions: hkl h+k=2n; h0l l=2n, and from subsequent least-squares refinement, the space group was determined to be C2/c (no. 4). The data were collected to a maximum 2θ value of 133.20°, at a temperature of 200±1 K.

Data Reduction

Frames were integrated with CrystalClear. A total of 15819 reflections were collected, of which 3060 were unique. Lorentz and polarization corrections were applied to the data. The linear absorption coefficient is 0.810 mm$^{-1}$ for Cu $K_\alpha$ radiation. An empirical absorption correction using CrystalClear was applied. Transmission coefficients ranged from 0.782 to 0.893. A secondary extinction correction was applied. The final coefficient, refined in least-squares, was 0.002450 (in absolute units). Intensities of equivalent reflections were averaged. The agreement factor for the averaging was 5% based on intensity.

Structure Solution and Refinement

The structure was solved by direct methods using SIR2004. The remaining atoms were located in succeeding difference Fourier syntheses. Some hydrogen atoms were refined independently, including all hydrogens residing on nitrogen or oxygen atoms. Other hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2) + (0.0594P)^2 + (1.8017P)]$, where $P = (F_o^2 + 2F_c^2)/3$.

Scattering factors were taken from the "International Tables for Crystallography". Of the 3060 reflections used in the refinements, only the reflections with $F_o^2 > 2\sigma(F_o^2)$ were used in calculating the fit residual, R. A total of 2449 reflections were used in the calculation. The final cycle of refinement included 260 variable parameters and converged (largest parameter shift was <0.01 times its estimated standard deviation) with unweighted and weighted agreement factors of:

$$R = \Sigma |F_o - F_c|/\Sigma F_o = 0.043$$

$$R_w = \sqrt{(\Sigma w(F_o^2 - F_c^2)^2/\Sigma w(F_o^2)^2)} = 0.111$$

The standard deviation of an observation of unit weight (goodness of fit) was 1.045. The highest peak in the final difference Fourier had a height of 0.29 e/Å$^3$. The minimum negative peak had a height of −0.20 e/Å$^3$. Note that the 0.29 e/Å$^3$ peak is in the position of a hydrogen residing on N12. While the residual electron density is much less than a full hydrogen atom, it likely indicates some hydrogen interaction with N12.

Calculated X-ray Powder Diffraction (XRPD) Pattern

A calculated XRPD pattern was generated for Cu radiation using PowderCell 2.3 and the atomic coordinates, space group, and unit cell parameters from the single crystal structure. Because the single crystal data are collected at low temperatures (200 K), peak shifts may be evident between the pattern calculated from low temperature data and the room temperature experimental powder diffraction pattern, particularly at high diffraction angles.

ORTEP and Packing Diagrams

The ORTEP diagram was prepared using the ORTEP III program within the PLATON software package. Atoms are represented by 50% probability anisotropic thermal ellipsoids. Packing diagrams were prepared using CAMERON modeling software. Additional figures were generated with the Mercury 3.0 visualization package. Hydrogen bonding is represented as dashed lines.

Results

The monoclinic cell parameters and calculated volume are: a=25.2302(10) Å, b=8.9582(3) Å, c=16.2196(13) Å, α=90.00°, β=107.744(17)°, γ=90.00°, V=3491.5(3) Å$^3$. The formula weight of the asymmetric unit in the crystal structure of minoxidil:benzoic acid monohydrate is 349.39 g mol$^{-1}$ with Z=8, resulting in a calculated density of 1.329 g cm$^{-3}$. The space group was determined to be C2/c. The space group and unit cell parameters are consistent with those determined previously from XRPD indexing. A summary of the crystal data and crystallographic data collection parameters are provided in Table 7 below.

TABLE 7

Crystal Data and Data Collection Parameters

| | |
|---|---|
| Formula | $C_{16}H_{23}N_5O_4$ |
| formula weight | 349.39 |
| space group | C2/c (No. 15) |
| a, Å | 25.2302(10) |
| b, Å | 8.9582(3) |
| c, Å | 16.2196(13) |
| β, deg | 107.744(17) |
| V, Å$^3$ | 3491.5(3) |
| Z | 8 |
| $d_{calc}$, g cm$^{-3}$ | 1.329 |
| crystal dimensions, mm | 0.20 × 0.18 × 0.14 |
| temperature, K | 200 |
| radiation (wavelength, Å) | Cu K$_\alpha$ (1.54184) |
| Monochromator | confocal optics |
| linear abs coef, mm$^{-1}$ | 0.810 |
| absorption correction applied | empirical [a] |
| transmission factors: min, max | 0.782, 0.893 |
| Diffractometer | Rigaku RAPID-II |
| h, k, l range | −29 to 30 −10 to 10 −14 to 19 |
| 2θ range, deg | 7.36-133.20 |
| mosaicity, deg | 0.66 |
| programs used | SHELXTL |
| $F_{000}$ | 1488.0 |
| weighting | $1/[\sigma^2(F_o^2) + (0.0610P)^2 + 1.8746P]$ where $P = (F_o^2 + 2F_c^2)/3$ |
| data collected | 16767 |
| unique data | 3060 |
| $R_{int}$ | 0.050 |
| data used in refinement | 3060 |
| cutoff used in R-factor calculations | $F_o^2 > 2.0\sigma(F_o^2)$ |
| data with I > 2.0σ(I) | 2449 |
| refined extinction coef | 0.0025 |
| number of variables | 260 |
| largest shift/esd in final cycle | 0.00 |
| $R(F_o)$ | 0.042 |
| $R_W(F_o^2)$ | 0.107 |
| goodness of fit | 1.027 |

[a] CrystalClear: *An Integrated Program for the Collection and Processing of Area Detector Data*, Rigaku Corporation, ©1997-2002.
[b] Flack, H. D. *Acta Cryst*, 1983 A39, 876.
[c] Hooft, R. W. W., Straver, L. H., and Spek, A. L. *J. Appl. Cryst.*, 2008, 41, 96-103

The quality of the structure obtained is high, as indicated by the fit residual, R of 0.043 (4.3%). R-values in the range of 0.02 to 0.06 are quoted for the most reliably determined structures.

Figure 19:
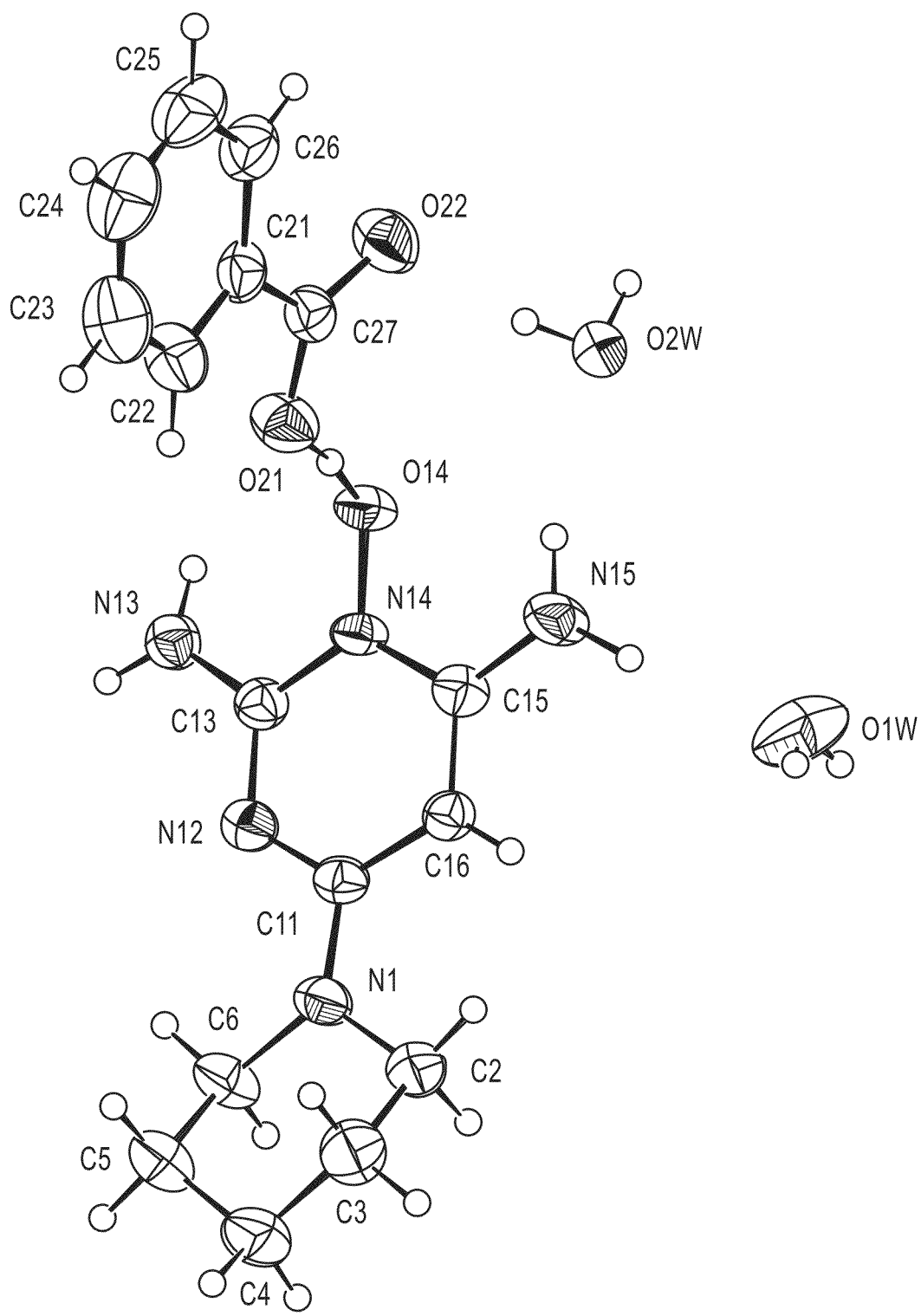
FIG. 19 is an ORTEP drawing of minoxidil:benzoic acid monohydrate.

An ORTEP drawing of minoxidil:benzoic acid monohydrate is shown in FIG. 19. The molecules observed in the asymmetric unit of the single crystal structure are consistent with the proposed molecular structures of minoxidl and benzoic acid. The asymmetric unit shown in FIG. 19 contains one minoxidil, one benzoic acid, and one water. There are two sites for water molecules that both reside on the 2-fold axis. Therefore, half of the water shown in FIG. 19 is symmetry generated, and therefore the stoichiometry is a monohydrate.

Figure 20:
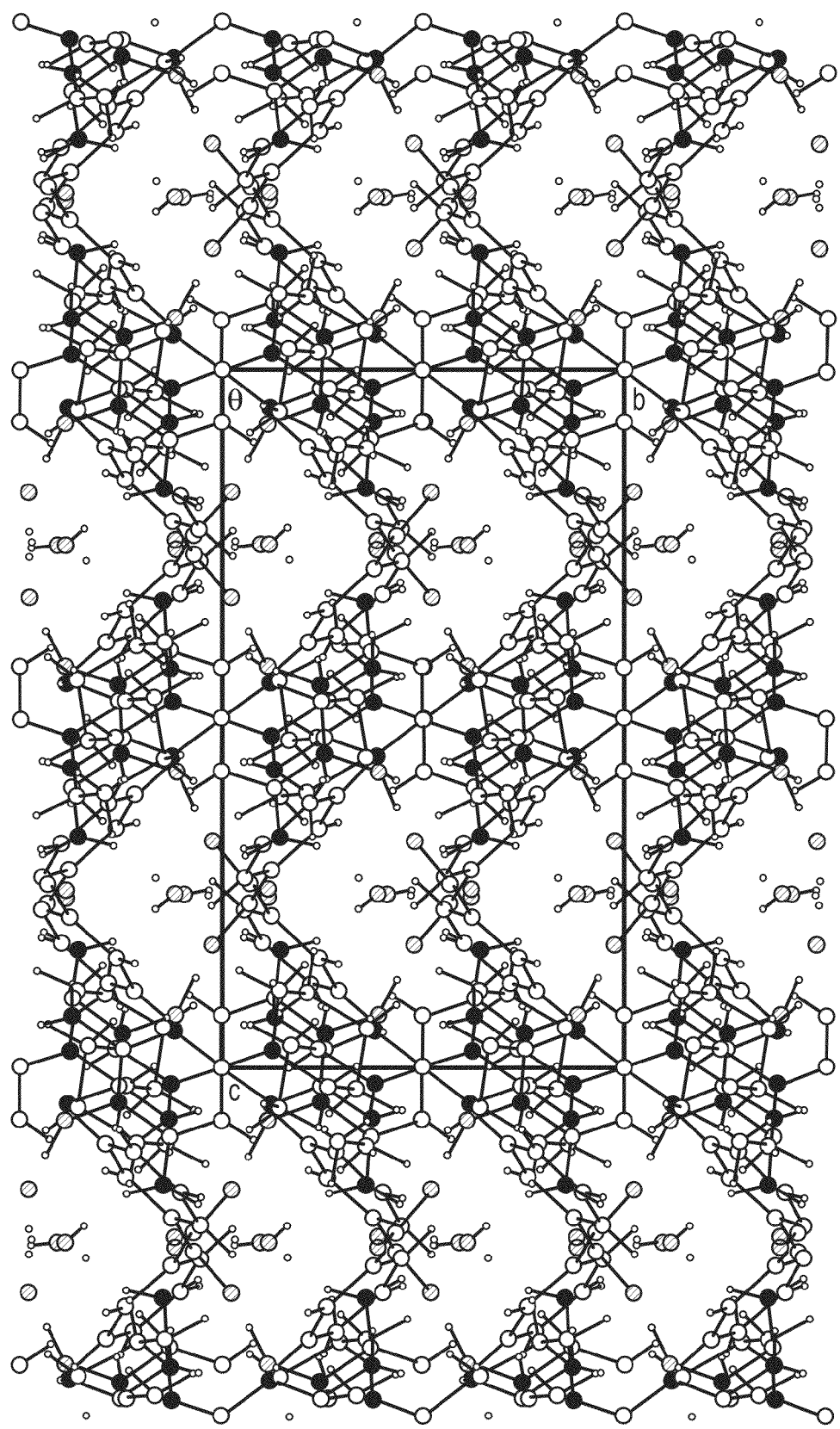
FIG. 20 is a packing diagram of minoxidil:benzoic acid monohydrate, viewed down the crystallographic a axis.
Figure 21:
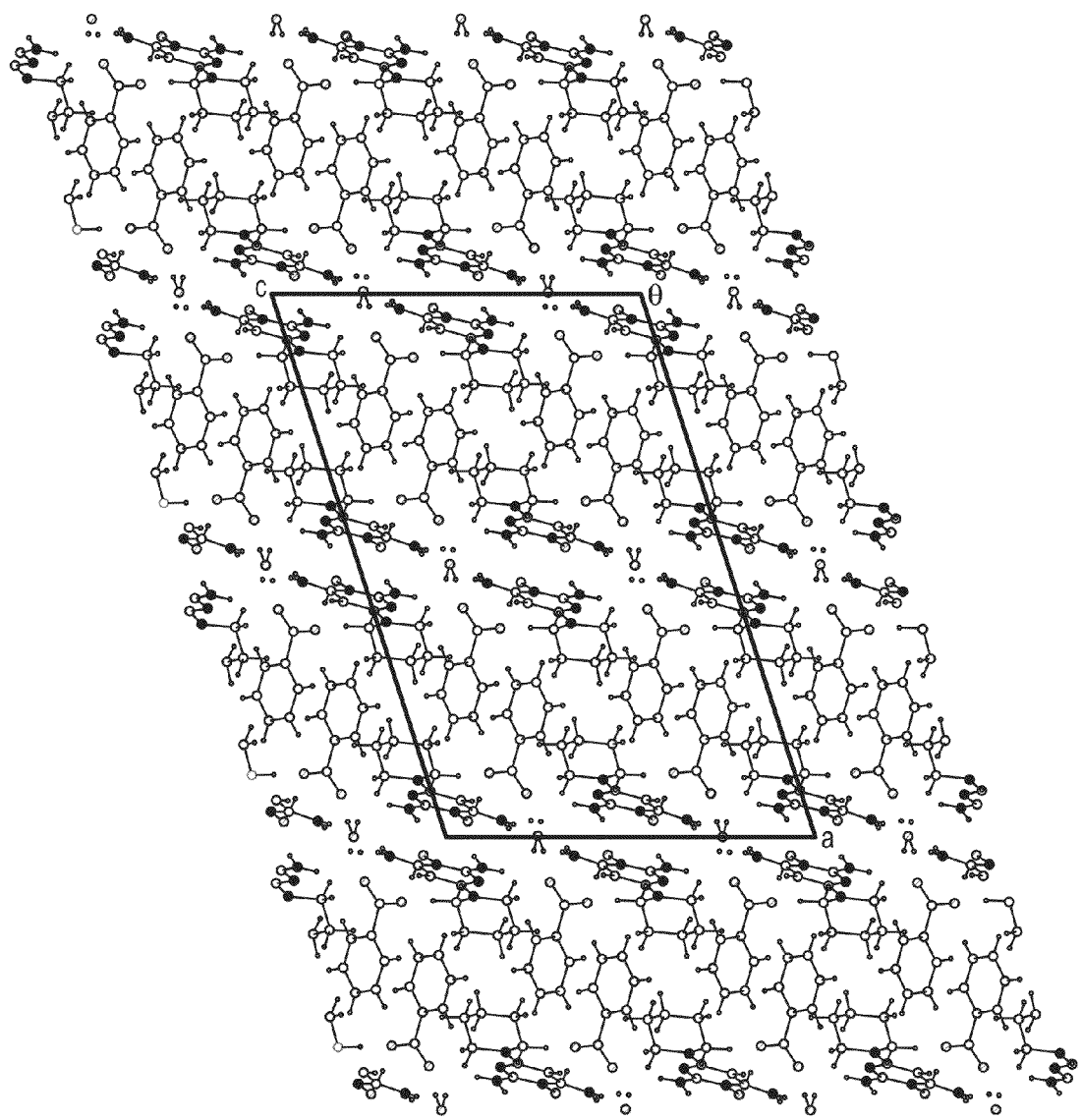
FIG. 21 is a packing diagram of minoxidil:benzoic acid monohydrate, viewed down the crystallographic b axis.
Figure 22:
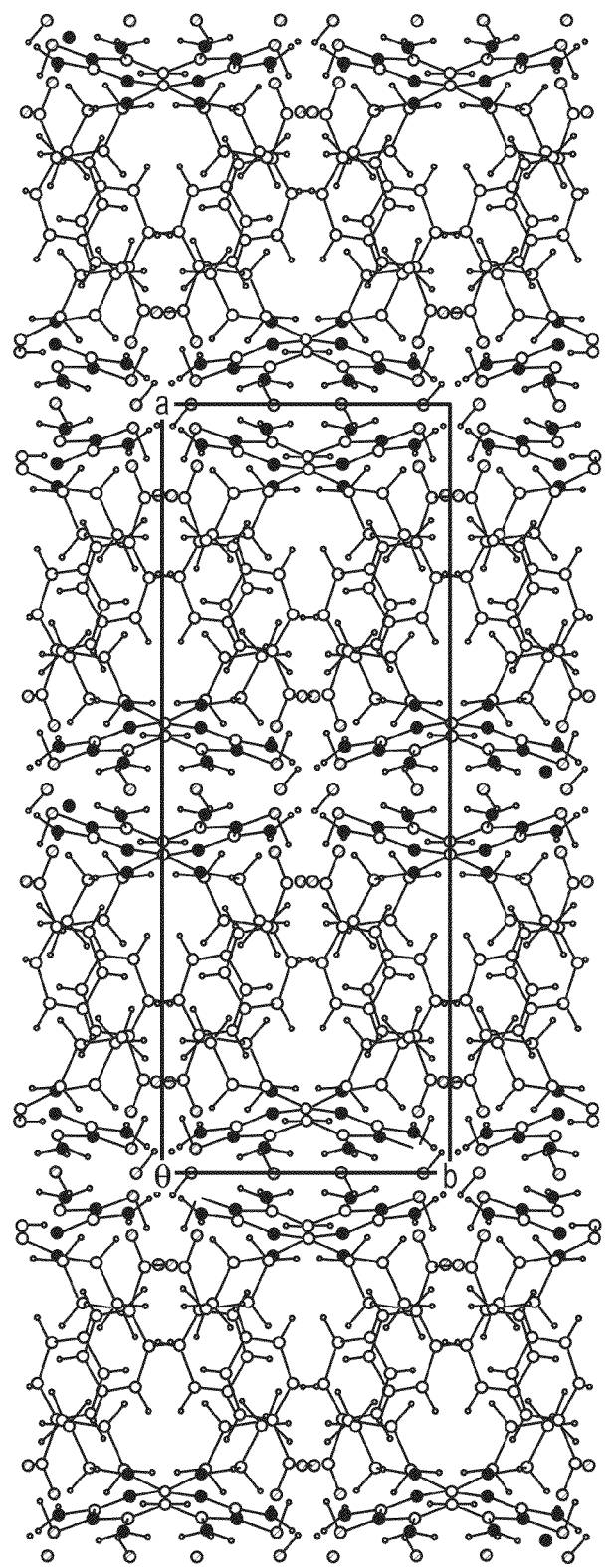
FIG. 22 is a packing diagram of minoxidil:benzoic acid monohydrate, viewed down the crystallographic c axis.
Figure 23:
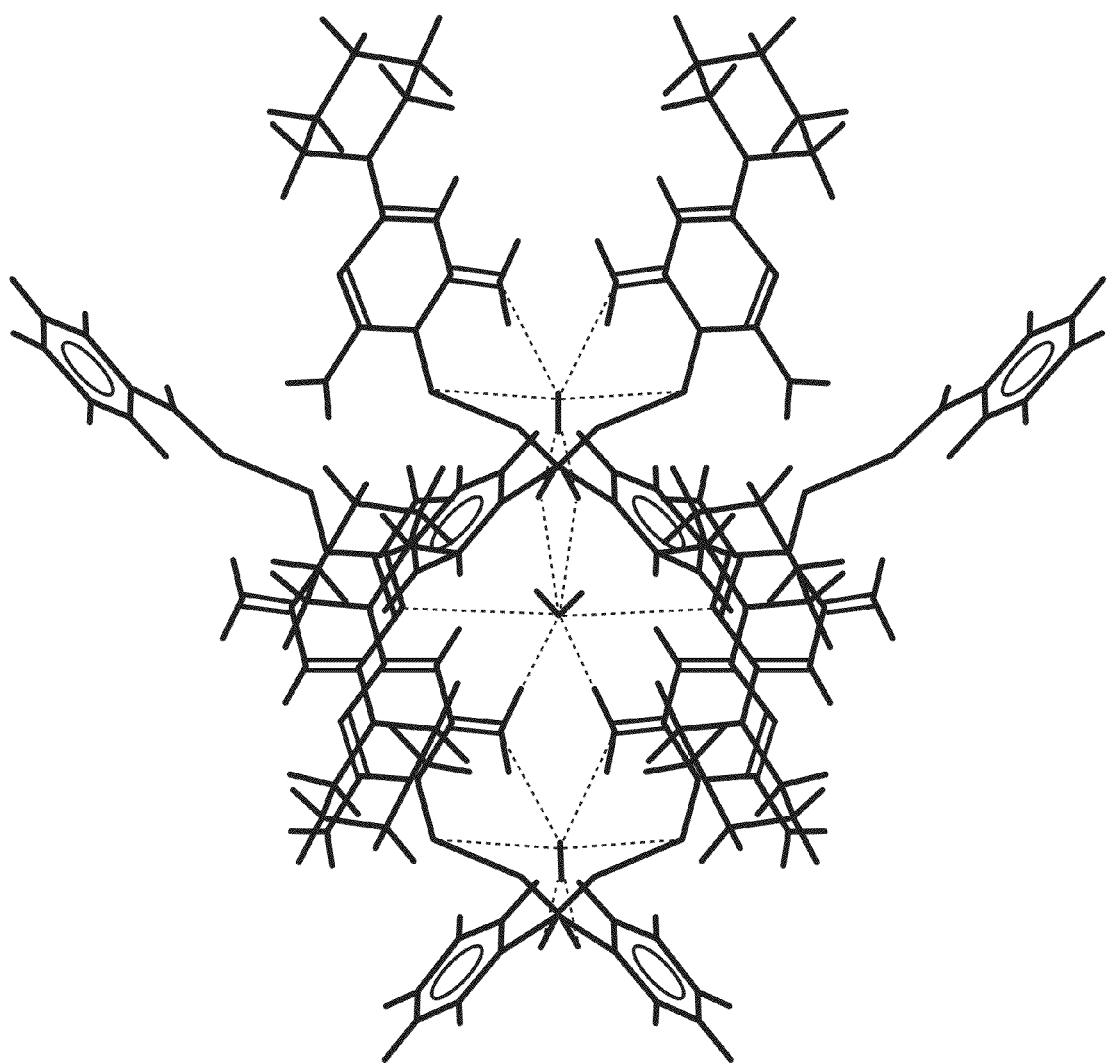
FIG. 23 is a graphical representation of potential hydrogen bonding points of contact around the water molecules in minoxidil:benzoic acid monohydrate.
Figure 24:
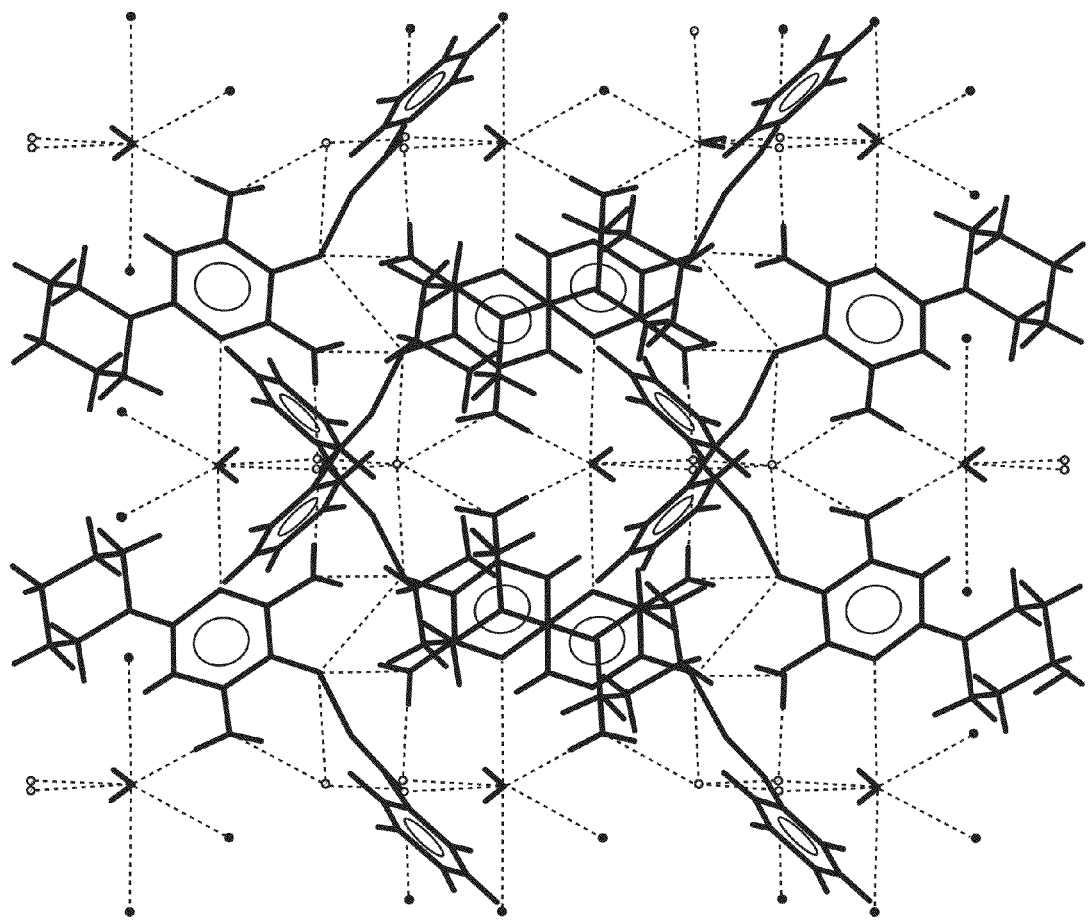
FIG. 24 is a graphical representation of hydrogen bonding in the bc plane of minoxidil:benzoic acid monohydrate.
Figure 25A:
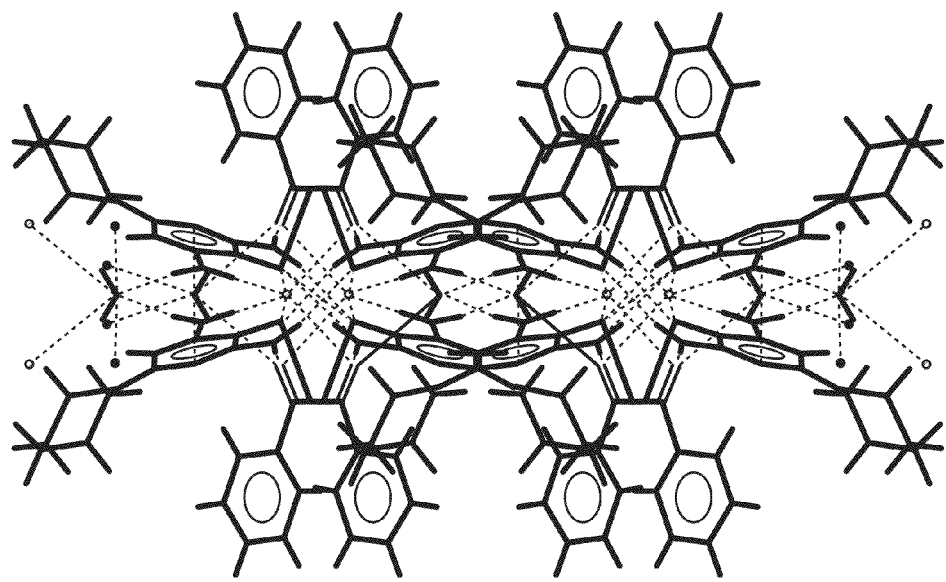
FIG. 25A is a graphical representation of hydrogen bonding along the b axis of minoxidil:benzoic acid monohydrate.
Figure 25B:
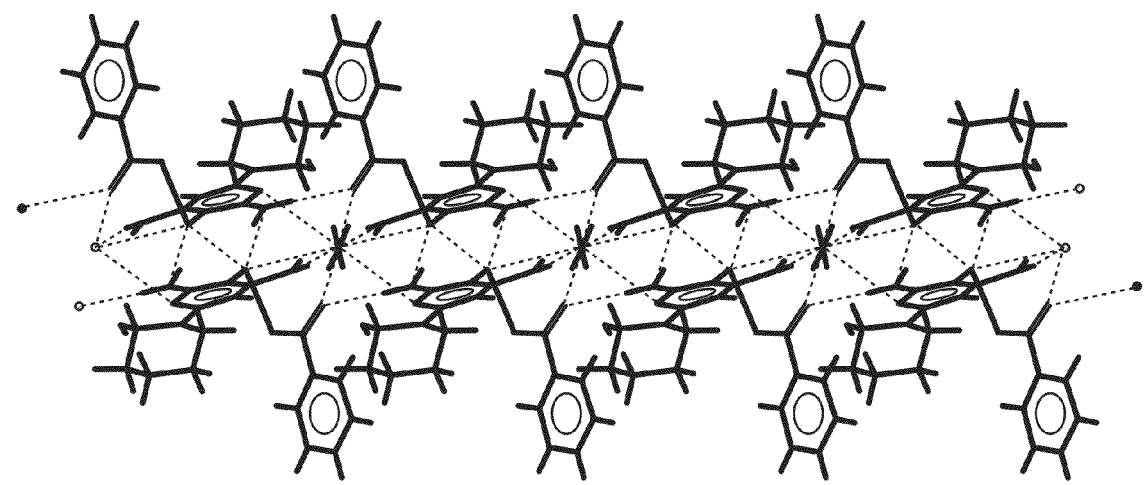
FIG. 25B is a graphical representation of hydrogen bonding along the c axis of minoxidil:benzoic acid monohydrate.
Figure 26:
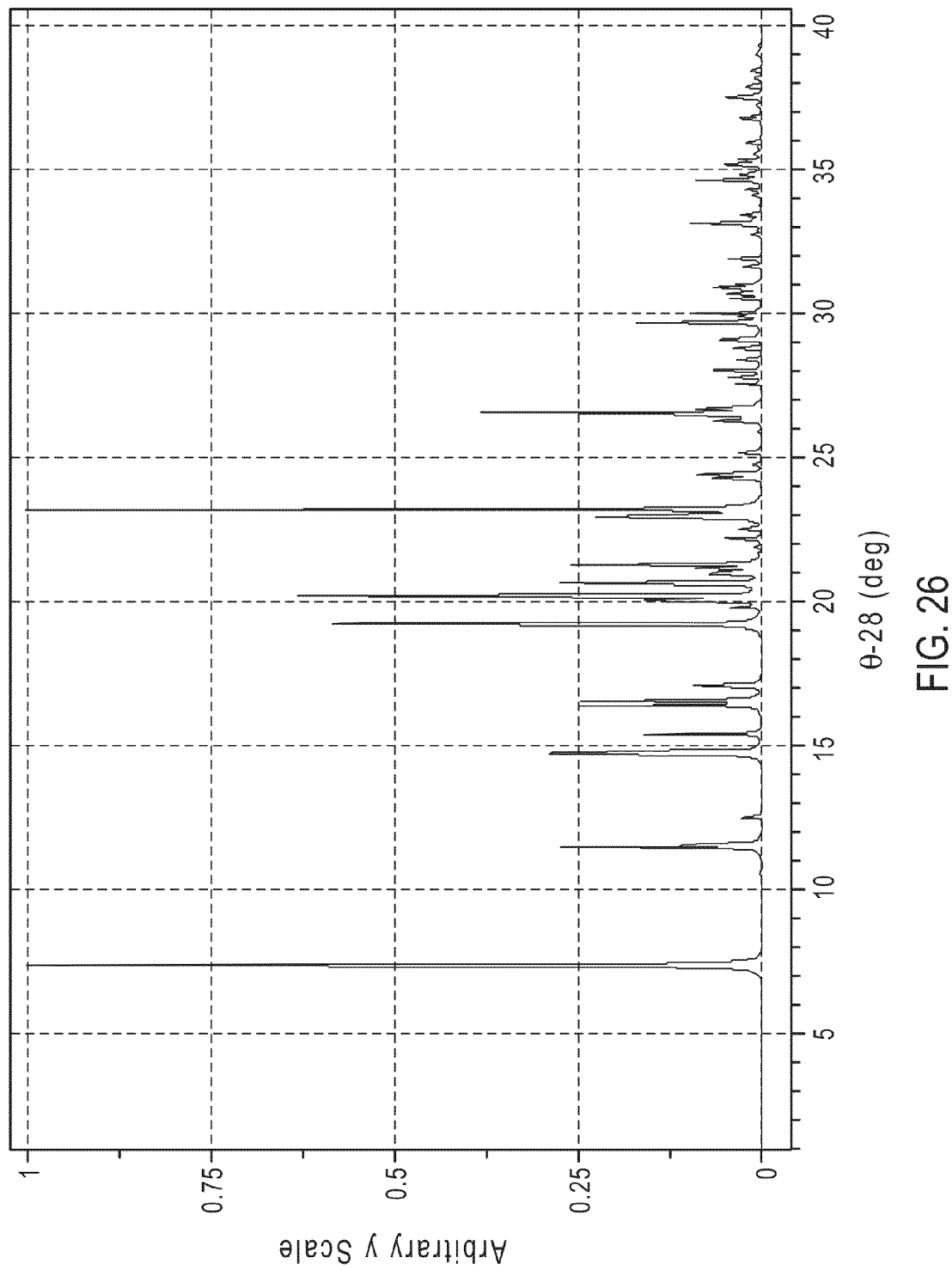
FIG. 26 is the calculated XRPD of minoxidil:benzoic acid monohydrate (single crystal analysis).

Packing diagrams viewed along the a, b, and c crystallographic axes are shown in FIGS. 20-22 respectively. A strong hydrogen bond occurs between the minoxidil N-oxide and the benzoic acid COOH group. The hydrogen was refined independently, and positioned 1.16 Å from the N-oxide and 1.28 Å from the COOH. Both of the water molecules are positioned with six potential hydrogen bonding contacts around them in nearly octahedral coordination, shown in FIG. 23. Assuming some interaction between the water and each of the potential contacts, the overall hydrogen bonding network is two-dimensional in the bc plane, depicted in FIG. 24. No hydrogen bonding occurs along the a axis (see FIGS. 25A-B).

FIG. 9 shows a calculated XRPD pattern of minoxidil:benzoic acid monohydrate, generated from the single crystal structure.

Tables of the positional parameters and their estimated deviations (Table 8), anisotropic temperature factor coefficients (Table 9), bond distances (Table 10), bond angles (Table 11), and hydrogen bonds and angles (Table 12) and torsion angles (Table 13) are provided below.

TABLE 8

Positional Parameters ($\times 10^4$) and Their Estimated Standard Deviations ($A^2 \times 10^3$)

| | x | y | z | U(eq) |
|---|---|---|---|---|
| O(14) | 313(1) | 1121(1) | 755(1) | 36(1) |
| O(1W) | 0 | 3840(3) | −2500 | 90(1) |
| O(21) | 1191(1) | 10228(1) | 1750(1) | 48(1) |
| O(22) | 811(1) | 8859(2) | 2566(1) | 55(1) |
| O(2W) | 0 | 9060(2) | −2500 | 42(1) |
| N(1) | 1078(1) | 6246(2) | −240(1) | 40(1) |
| N(12) | 786(1) | 3790(2) | −522(1) | 36(1) |
| N(13) | 542(1) | 1287(2) | −729(1) | 41(1) |
| N(14) | 484(1) | 2455(1) | 498(1) | 31(1) |
| N(15) | 328(1) | 3545(2) | 1685(1) | 45(1) |
| C(2) | 1161(1) | 7628(2) | 268(1) | 51(1) |
| C(3) | 1712(1) | 8333(2) | 314(1) | 54(1) |
| C(4) | 1777(1) | 8565(2) | −572(1) | 55(1) |
| C(5) | 1693(1) | 7104(2) | −1063(1) | 50(1) |
| C(6) | 1138(1) | 6412(2) | −1106(1) | 46(1) |
| C(11) | 848(1) | 5023(2) | −4(1) | 32(1) |
| C(13) | 604(1) | 2536(2) | −263(1) | 32(1) |
| C(15) | 496(1) | 3702(2) | 989(1) | 33(1) |
| C(16) | 687(1) | 5003(2) | 739(1) | 32(1) |
| C(21) | 1793(1) | 8762(2) | 2844(1) | 39(1) |
| C(22) | 2258(1) | 9444(2) | 2731(1) | 52(1) |
| C(23) | 2786(1) | 8975(3) | 3207(2) | 66(1) |
| C(24) | 2848(1) | 7820(3) | 3792(2) | 68(1) |
| C(25) | 2389(1) | 7139(2) | 3904(1) | 62(1) |
| C(26) | 1860(1) | 7606(2) | 3435(1) | 49(1) |
| C(27) | 1219(1) | 9305(2) | 2359(1) | 38(1) |
| H(14) | 716(11) | 660(30) | 1253(17) | 91(8) |
| H(2A) | 1150 | 7405 | 860 | 61 |
| H(2B) | 856 | 8336 | −2 | 61 |
| H(3A) | 2018 | 7686 | 659 | 65 |
| H(3B) | 1744 | 9308 | 613 | 65 |
| H(4A) | 2153 | 8962 | −514 | 65 |
| H(4B) | 1500 | 9305 | −897 | 65 |
| H(5A) | 1997 | 6405 | −773 | 60 |
| H(5B) | 1710 | 7281 | −1658 | 60 |
| H(6A) | 834 | 7050 | −1463 | 55 |
| H(6B) | 1106 | 5421 | −1387 | 55 |
| H(16) | 683(8) | 5780(20) | 1029(13) | 45(5) |
| H(22) | 2215 | 10235 | 2326 | 63 |
| H(23) | 3104 | 9449 | 3131 | 79 |
| H(24) | 3210 | 7496 | 4117 | 81 |
| H(25) | 2434 | 6343 | 4306 | 74 |
| H(26) | 1542 | 7134 | 3518 | 58 |
| H(1W) | 270(20) | 3390(60) | −2280(40) | 240(30) |
| H(2W) | 276(10) | 9700(30) | −2542(16) | 84(8) |
| H(131) | 627(8) | 1280(20) | −1206(14) | 51(6) |
| H(132) | 338(9) | 570(20) | −616(13) | 53(6) |
| H(151) | 211(8) | 2650(30) | 1805(13) | 55(6) |
| H(152) | 258(8) | 4410(30) | 1952(14) | 59(6) |

Starred atoms were refined isotropically
$U_{eq} = (1/3)\Sigma_i\Sigma_j U_{ij}a^*_i a^*_j \cdot a_i \cdot a_j$
Hydrogen atoms are included in calculation of structure factors but not refined

TABLE 9

Anisotropic Displacement Factor Coefficients - U's

| | U11 | U22 | U33 | U23 | U13 | U12 |
|---|---|---|---|---|---|---|
| O(14) | 45(1) | 31(1) | 32(1) | 3(1) | 11(1) | −9(1) |
| O(1W) | 116(2) | 41(1) | 108(2) | 0 | 24(2) | 0 |
| O(21) | 50(1) | 53(1) | 41(1) | 14(1) | 12(1) | 4(1) |
| O(22) | 45(1) | 69(1) | 55(1) | 23(1) | 22(1) | 14(1) |
| O(2W) | 51(1) | 37(1) | 46(1) | 0 | 25(1) | 0 |
| N(1) | 55(1) | 33(1) | 39(1) | 0(1) | 23(1) | −8(1) |

TABLE 9-continued

Anisotropic Displacement Factor Coefficients - U's

| | U11 | U22 | U33 | U23 | U13 | U12 |
|---|---|---|---|---|---|---|
| N(12) | 41(1) | 34(1) | 34(1) | 3(1) | 14(1) | −1(1) |
| N(13) | 58(1) | 36(1) | 35(1) | −3(1) | 21(1) | −6(1) |
| N(14) | 37(1) | 28(1) | 28(1) | 3(1) | 10(1) | −4(1) |
| N(15) | 69(1) | 37(1) | 33(1) | −4(1) | 23(1) | −11(1) |
| C(2) | 68(1) | 32(1) | 64(1) | −6(1) | 38(1) | −8(1) |
| C(3) | 63(1) | 42(1) | 62(1) | −11(1) | 26(1) | −14(1) |
| C(4) | 52(1) | 49(1) | 69(1) | 6(1) | 28(1) | −12(1) |
| C(5) | 52(1) | 57(1) | 47(1) | 6(1) | 24(1) | −8(1) |
| C(6) | 54(1) | 52(1) | 36(1) | 7(1) | 17(1) | −9(1) |
| C(11) | 31(1) | 31(1) | 31(1) | 4(1) | 8(1) | 0(1) |
| C(13) | 32(1) | 34(1) | 29(1) | 4(1) | 9(1) | 2(1) |
| C(15) | 34(1) | 35(1) | 27(1) | 0(1) | 6(1) | −3(1) |
| C(16) | 38(1) | 28(1) | 29(1) | −3(1) | 10(1) | −4(1) |
| C(21) | 43(1) | 44(1) | 32(1) | −3(1) | 15(1) | 7(1) |
| C(22) | 50(1) | 65(1) | 45(1) | 2(1) | 18(1) | 2(1) |
| C(23) | 42(1) | 88(2) | 66(1) | −8(1) | 14(1) | −1(1) |
| C(24) | 47(1) | 79(2) | 64(1) | −10(1) | −2(1) | 17(1) |
| C(25) | 66(1) | 55(1) | 56(1) | 6(1) | 5(1) | 21(1) |
| C(26) | 52(1) | 46(1) | 48(1) | 3(1) | 15(1) | 11(1) |
| C(27) | 44(1) | 41(1) | 33(1) | 1(1) | 15(1) | 5(1) |

The form of the anisotropic temperature factor is:
$\exp[-2\pi^2 h^2 a^{*2} U(1,1) + k^2 b^{*2} U(2,2) + l^2 c^{*2} U(3,3) + 2hka^*b^*U(1,2) + 2hla^*c^*U(1,3) + 2klb^*c^*U(2,3)]$ where $a^*$, $b^*$, and $c^*$ are reciprocal lattice constants.

TABLE 10

Bond Distances in Angstroms

| Bond | Distance(Å) |
|---|---|
| O(14)—N(14) | 1.3772(15) |
| O(14)—H(14) | 1.16(3) |
| O(1W)—H(1W) | 0.77(5) |
| O(21)—C(27) | 1.274(2) |
| O(22)—C(27) | 1.241(2) |
| O(2W)—H(2W) | 0.92(2) |
| N(1)—C(11) | 1.349(2) |
| N(1)—C(6) | 1.465(2) |
| N(1)—C(2) | 1.466(2) |
| N(12)—C(13) | 1.329(2) |
| N(12)—C(11) | 1.368(2) |
| N(13)—C(13) | 1.333(2) |
| N(13)—H(131) | 0.86(2) |
| N(13)—H(132) | 0.88(2) |
| N(14)—C(13) | 1.3583(19) |
| N(14)—C(15) | 1.367(2) |
| N(15)—C(15) | 1.328(2) |
| N(15)—H(151) | 0.89(2) |
| N(15)—H(152) | 0.93(2) |
| C(2)—C(3) | 1.508(3) |
| C(2)—H(2A) | 0.9900 |
| C(2)—H(2B) | 0.9900 |
| C(3)—C(4) | 1.509(3) |
| C(3)—H(3A) | 0.9900 |
| C(3)—H(3B) | 0.9900 |
| C(4)—C(5) | 1.514(3) |
| C(4)—H(4A) | 0.9900 |
| C(4)—H(4B) | 0.9900 |
| C(5)—C(6) | 1.515(2) |
| C(5)—H(5A) | 0.9900 |
| C(5)—H(5B) | 0.9900 |
| C(6)—H(6A) | 0.9900 |
| C(6)—H(6B) | 0.9900 |
| C(11)—C(16) | 1.385(2) |
| C(15)—C(16) | 1.369(2) |
| C(16)—H(16) | 0.84(2) |
| C(21)—C(22) | 1.384(3) |
| C(21)—C(26) | 1.386(2) |
| C(21)—C(27) | 1.503(2) |
| C(22)—C(23) | 1.384(3) |
| C(22)—H(22) | 0.9500 |
| C(23)—C(24) | 1.380(3) |
| C(23)—H(23) | 0.9500 |
| C(24)—C(25) | 1.369(3) |

TABLE 10-continued

Bond Distances in Angstroms

| Bond | Distance(Å) |
| --- | --- |
| C(24)—H(24) | 0.9500 |
| C(25)—C(26) | 1.385(3) |
| C(25)—H(25) | 0.9500 |
| C(26)—H(26) | 0.9500 |

Numbers in parentheses are estimated standard deviations in the least significant digits.

TABLE 11

Bond Angles in Degrees

| Angle | Degree(°) |
| --- | --- |
| N(14)—O(14)—H(14) | 103.1(13) |
| C(11)—N(1)—C(6) | 122.26(14) |
| C(11)—N(1)—C(2) | 121.75(14) |
| C(6)—N(1)—C(2) | 114.47(14) |
| C(13)—N(12)—C(11) | 118.29(13) |
| C(13)—N(13)—H(131) | 119.9(13) |
| C(13)—N(13)—H(132) | 118.1(14) |
| H(131)—N(13)—H(132) | 120.2(19) |
| C(13)—N(14)—C(15) | 120.91(13) |
| C(13)—N(14)—O(14) | 119.89(12) |
| C(15)—N(14)—O(14) | 119.06(12) |
| C(15)—N(15)—H(151) | 119.5(13) |
| C(15)—N(15)—H(152) | 117.4(13) |
| H(151)—N(15)—H(152) | 121.5(19) |
| N(1)—C(2)—C(3) | 110.72(15) |
| N(1)—C(2)—H(2A) | 109.5 |
| C(3)—C(2)—H(2A) | 109.5 |
| N(1)—C(2)—H(2B) | 109.5 |
| C(3)—C(2)—H(2B) | 109.5 |
| H(2A)—C(2)—H(2B) | 108.1 |
| C(2)—C(3)—C(4) | 112.05(17) |
| C(2)—C(3)—H(3A) | 109.2 |
| C(4)—C(3)—H(3A) | 109.2 |
| C(2)—C(3)—H(3B) | 109.2 |
| C(4)—C(3)—H(3B) | 109.2 |
| H(3A)—C(3)—H(3B) | 107.9 |
| C(3)—C(4)—C(5) | 110.12(15) |
| C(3)—C(4)—H(4A) | 109.6 |
| C(5)—C(4)—H(4A) | 109.6 |
| C(3)—C(4)—H(4B) | 109.6 |
| C(5)—C(4)—H(4B) | 109.6 |
| H(4A)—C(4)—H(4B) | 108.2 |
| C(4)—C(5)—C(6) | 110.84(16) |
| C(4)—C(5)—H(5A) | 109.5 |
| C(6)—C(5)—H(5A) | 109.5 |
| C(4)—C(5)—H(5B) | 109.5 |
| C(6)—C(5)—H(5B) | 109.5 |
| H(5A)—C(5)—H(5B) | 108.1 |
| N(1)—C(6)—C(5) | 111.23(14) |
| N(1)—C(6)—H(6A) | 109.4 |
| C(5)—C(6)—H(6A) | 109.4 |
| N(1)—C(6)—H(6B) | 109.4 |
| C(5)—C(6)—H(6B) | 109.4 |
| H(6A)—C(6)—H(6B) | 108.0 |
| N(1)—C(11)—N(12) | 117.40(14) |
| N(1)—C(11)—C(16) | 121.59(14) |
| N(12)—C(11)—C(16) | 121.00(14) |
| N(12)—C(13)—N(13) | 121.42(15) |
| N(12)—C(13)—N(14) | 121.80(14) |
| N(13)—C(13)—N(14) | 116.76(14) |
| N(15)—C(15)—N(14) | 116.94(14) |
| N(15)—C(15)—C(16) | 125.00(15) |
| N(14)—C(15)—C(16) | 118.06(14) |
| C(15)—C(16)—C(11) | 119.47(15) |
| C(15)—C(16)—H(16) | 118.2(13) |
| C(11)—C(16)—H(16) | 122.2(13) |
| C(22)—C(21)—C(26) | 119.43(17) |
| C(22)—C(21)—C(27) | 120.65(16) |
| C(26)—C(21)—C(27) | 119.87(16) |
| C(21)—C(22)—C(23) | 120.2(2) |
| C(21)—C(22)—H(22) | 119.9 |

TABLE 11-continued

Bond Angles in Degrees

| Angle | Degree(°) |
| --- | --- |
| C(23)—C(22)—H(22) | 119.9 |
| C(24)—C(23)—C(22) | 119.9(2) |
| C(24)—C(23)—H(23) | 120.0 |
| C(22)—C(23)—H(23) | 120.0 |
| C(25)—C(24)—C(23) | 120.12(19) |
| C(25)—C(24)—H(24) | 119.9 |
| C(23)—C(24)—H(24) | 119.9 |
| C(24)—C(25)—C(26) | 120.4(2) |
| C(24)—C(25)—H(25) | 119.8 |
| C(26)—C(25)—H(25) | 119.8 |
| C(25)—C(26)—C(21) | 120.0(2) |
| C(25)—C(26)—H(26) | 120.0 |
| C(21)—C(26)—H(26) | 120.0 |
| O(22)—C(27)—O(21) | 124.36(15) |
| O(22)—C(27)—C(21) | 120.04(15) |
| O(21)—C(27)—C(21) | 115.60(15) |

Numbers in parentheses are estimated standard deviations in the least significant digits.

TABLE 12

Hydrogen Bond Distances in Angstroms and Angles in Degrees

| D | H | A | D-H | A-H | D-A | D-H-A |
| --- | --- | --- | --- | --- | --- | --- |
| O(1W) | H(1W) | O(22) | 0.77 | 2.49 | 3.15 | 144 |
| O(2W) | H(2W) | O(22) | 0.92 | 1.84 | 2.75 | 169 |
| O(14) | H(14) | O(21) | 1.16 | 1.28 | 2.44 | 174 |
| N(13) | H(131) | O(22) | 0.86 | 2.18 | 3.04 | 177 |
| N(13) | H(132) | O(14) | 0.88 | 2.30 | 2.65 | 104 |
| N(13) | H(132) | O(14) | 0.88 | 2.19 | 3.04 | 162 |
| N(15) | H(151) | O(2W) | 0.89 | 2.07 | 2.92 | 160 |
| N(15) | H(151) | O(14) | 0.89 | 2.26 | 2.64 | 105 |
| N(15) | N(152) | O(1W) | 0.93 | 2.00 | 2.93 | 172 |

Numbers in parentheses are estimated standard deviations in the least significant digits.

TABLE 13

Torsion Angles in Degrees

| Angle | Degree(°) |
| --- | --- |
| C(11)—N(1)—C(2)—C(3) | 140.07(17) |
| C(6)—N(1)—C(2)—C(3) | −53.7(2) |
| N(1)—C(2)—C(3)—C(4) | 53.7(2) |
| C(2)—C(3)—C(4)—C(5) | −55.3(2) |
| C(3)—C(4)—C(5)—C(6) | 55.1(2) |
| C(11)—N(1)—C(6)—C(5) | −139.36(17) |
| C(2)—N(1)—C(6)—C(5) | 54.5(2) |
| C(4)—C(5)—C(6)—N(1) | −54.4(2) |
| C(6)—N(1)—C(11)—N(12) | 14.6(2) |
| C(2)—N(1)—C(11)—N(12) | 179.76(15) |
| C(6)—N(1)—C(11)—C(16) | −166.21(15) |
| C(2)—N(1)—C(11)—C(16) | −1.0(2) |
| C(13)—N(12)—C(11)—N(1) | 174.44(14) |
| C(13)—N(12)—C(11)—C(16) | −4.8(2) |
| C(11)—N(12)—C(13)—N(13) | −178.94(14) |
| C(11)—N(12)—C(13)—N(14) | −0.5(2) |
| C(15)—N(14)—C(13)—N(12) | 6.4(2) |
| O(14)—N(14)—C(13)—N(12) | −177.95(13) |
| C(15)—N(14)—C(13)—N(13) | −175.12(14) |
| O(14)—N(14)—C(13)—N(13) | 0.6(2) |
| C(13)—N(14)—C(15)—N(15) | 174.49(14) |
| O(14)—N(14)—C(15)—N(15) | −1.2(2) |
| C(13)—N(14)—C(15)—C(16) | −6.7(2) |
| O(14)—N(14)—C(15)—C(16) | 177.56(13) |
| N(15)—C(15)—C(16)—C(11) | −179.79(16) |
| N(14)—C(15)—C(16)—C(11) | 1.5(2) |
| N(1)—C(11)—C(16)—C(15) | −174.94(14) |
| N(12)—C(11)—C(16)—C(15) | 4.2(2) |
| C(26)—C(21)—C(22)—C(23) | −0.1(3) |
| C(27)—C(21)—C(22)—C(23) | 177.32(18) |

TABLE 13-continued

Torsion Angles in Degrees

| Angle | Degree(°) |
|---|---|
| C(21)—C(22)—C(23)—C(24) | 0.4(3) |
| C(22)—C(23)—C(24)—C(25) | −0.2(3) |
| C(23)—C(24)—C(25)—C(26) | −0.2(3) |
| C(24)—C(25)—C(26)—C(21) | 0.4(3) |
| C(22)—C(21)—C(26)—C(25) | −0.2(3) |
| C(27)—C(21)—C(26)—C(25) | −177.72(17) |
| C(22)—C(21)—C(27)—O(22) | −168.08(17) |
| C(26)—C(21)—C(27)—O(22) | 9.4(2) |
| C(22)—C(21)—C(27)—O(21) | 11.5(2) |
| C(26)—C(21)—C(27)—O(21) | −171.06(16) |

Numbers in parentheses are estimated standard deviations in the least significant digits.

The invention claimed is:

1. A process for making a cocrystal of progesterone and a coformer comprising combining progesterone dissolved in a solvent solution with the coformer dissolved in the solvent solution wherein the solubilities of progesterone and the coformer in the solvent solution are each of a value sufficiently similar to form a cocrystal of progesterone and the coformer as a single crystal phase, and precipitating a cocrystal from the solvent solution to form a cocrystal of progesterone and the coformer.

2. The process of claim 1 wherein the coformer is vanillic acid.

3. The process of claim 2 wherein the solvent solution comprises heptane and isopropyl alcohol.

4. The process of claim 3 wherein the ratio of isopropyl alcohol to heptane is about 50:50.

5. The process of claim 2, wherein the cocrystal of progesterone and vanillic acid is prepared by cooling of a solution.

6. The process of claim 1 wherein the cocrystal of progesterone and the coformer is prepared by cooling of a solution.

7. The process of claim 1, further comprising the step of seeding the solvent solution.

8. The process of claim 7 wherein the seed is a cocrystal of progesterone and vanillic acid.

9. The process of claim 7 wherein the seed is a cocrystal of progesterone and the coformer.

10. The process of claim 1 wherein the coformer is cinnamic acid.

11. The process of claim 10 wherein the solvent solution comprises ethyl acetate and heptane.

12. The process of claim 11 wherein the ratio of ethyl acetate to heptane is about 25:75.

13. The process of claim 10, wherein the cocrystal of progesterone and cinnamic acid is prepared by cooling of a solution.

14. The process of claim 10, further comprising the step of seeding the solvent solution.

15. The process of claim 14 wherein the seed is a cocrystal of progesterone and cinnamic acid.

* * * * *